(12) United States Patent
Rapaport et al.

(10) Patent No.: US 9,510,855 B2
(45) Date of Patent: Dec. 6, 2016

(54) METHOD AND APPARATUS FOR ALLOWING BLOOD FLOW THROUGH AN OCCLUDED VESSEL

(75) Inventors: Avraham Rapaport, Tel-Aviv (IL); Gilad Cibulski, Zur-Moshe (IL)

(73) Assignee: Perflow Medical Ltd., Tel-Aviv (IL)

( * ) Notice: Subject to any disclaimer, the term of this patent is extended or adjusted under 35 U.S.C. 154(b) by 206 days.

(21) Appl. No.: 13/378,053

(22) PCT Filed: Jun. 15, 2010

(86) PCT No.: PCT/IL2010/000470
§ 371 (c)(1),
(2), (4) Date: Dec. 14, 2011

(87) PCT Pub. No.: WO2010/146581
PCT Pub. Date: Dec. 23, 2010

(65) Prior Publication Data
US 2012/0089216 A1    Apr. 12, 2012

Related U.S. Application Data

(60) Provisional application No. 61/186,942, filed on Jun. 15, 2009.

(51) Int. Cl.
*A61B 17/3207* (2006.01)
*A61F 2/86* (2013.01)
(Continued)

(52) U.S. Cl.
CPC ......... *A61B 17/320725* (2013.01); *A61F 2/86* (2013.01); *A61M 29/02* (2013.01);
(Continued)

(58) Field of Classification Search
CPC ............ A61B 17/221; A61B 17/32075; A61B 2017/2215; A61B 2017/00893; A61B 2017/22034;A61B 17/320725; A61F 2/01; A61F 2/86; A61F 2/88; A61F 2230/0078; A61F 2250/0059; A61F 2220/005; A61F 2220/0058; A61F 2220/0075; A61M 29/02
(Continued)

(56) References Cited

U.S. PATENT DOCUMENTS 4,468,216 A    8/1984  Muto
4,611,594 A    9/1986  Grayhack et al.
(Continued)

FOREIGN PATENT DOCUMENTS

EP    0914807 A2    5/1999
EP    1437097 A1    7/2004
(Continued)

OTHER PUBLICATIONS

M. E. Kelly et al., "Recanalization of an Acute Middle Cerebral Artery Occlusion Using a Self-Expanding constrainable, Intracranial Microstent as a Temporary Endovascular Bypass", American Heart Association, Inc., Stroke, Jun. 2008.
(Continued)

*Primary Examiner* — David C Eastwood

(57) ABSTRACT

A device arranged to sustain and/or provide at least partial patency of a small blood vessel exhibiting an occlusion, the device constituted of a tubular body expandable from a first small diameter state for manipulation to, and through, the occlusion of the small blood vessel and a second large diameter state, the inner dimensions of the second large diameter state being no more than 50% of the diameter of the small blood vessel at the occlusion location, the device presenting a conduit for blood flow through the occlusion when in the large diameter state. In one embodiment the small blood vessel is an intracranial blood vessel.

31 Claims, 17 Drawing Sheets

(51) Int. Cl.

| | | |
|---|---|---|
| *A61M 29/02* | (2006.01) | |
| *A61B 17/221* | (2006.01) | |
| *A61B 17/00* | (2006.01) | |
| *A61B 17/22* | (2006.01) | |
| *A61F 2/01* | (2006.01) | |
| *A61F 2/88* | (2006.01) | |

(52) U.S. Cl.
CPC ... *A61B 17/221* (2013.01); *A61B 2017/00893* (2013.01); *A61B 2017/2215* (2013.01); *A61B 2017/22034* (2013.01); *A61F 2/01* (2013.01); *A61F 2/88* (2013.01); *A61F 2220/005* (2013.01); *A61F 2220/0058* (2013.01); *A61F 2220/0075* (2013.01); *A61F 2230/0078* (2013.01); *A61F 2250/0059* (2013.01)

(58) Field of Classification Search
USPC .............................. 606/191, 194, 198, 200, 110–115,606/127–128, 159; 623/1.11–1.15, 1.17
See application file for complete search history.

(56) References Cited

U.S. PATENT DOCUMENTS

| | | | |
|---|---|---|---|
| 4,650,466 A * | 3/1987 | Luther | 604/95.04 |
| 4,666,426 A | 5/1987 | Aigner | |
| 4,804,358 A | 2/1989 | Karcher et al. | |
| 4,850,969 A | 7/1989 | Jackson | |
| 4,921,483 A | 5/1990 | Wijay et al. | |
| 5,066,282 A | 11/1991 | Wijay et al. | |
| 5,090,960 A | 2/1992 | Don Michael | |
| 5,106,363 A | 4/1992 | Nobuyoshi | |
| 5,149,321 A | 9/1992 | Klatz et al. | |
| 5,158,540 A | 10/1992 | Wijay et al. | |
| 5,184,627 A | 2/1993 | De Toledo | |
| 5,186,713 A | 2/1993 | Raible | |
| 5,403,274 A | 4/1995 | Cannon | |
| 5,407,424 A | 4/1995 | LaFontaine et al. | |
| 5,425,723 A | 6/1995 | Wang | |
| 5,451,207 A | 9/1995 | Yock | |
| 5,462,523 A | 10/1995 | Samson et al. | |
| 5,531,715 A | 7/1996 | Engelson et al. | |
| 5,584,804 A | 12/1996 | Klatz et al. | |
| 5,643,228 A | 7/1997 | Schucart et al. | |
| 5,653,684 A | 8/1997 | Laptewicz et al. | |
| 5,972,019 A | 10/1999 | Engelson et al. | |
| 6,044,845 A | 4/2000 | Lewis | |
| 6,066,158 A | 5/2000 | Engelson et al. | |
| 6,139,517 A | 10/2000 | Macoviak et al. | |
| 6,149,665 A | 11/2000 | Gabbay | |
| 6,258,118 B1 | 7/2001 | Baum et al. | |
| 6,295,990 B1 | 10/2001 | Lewis et al. | |
| 6,481,439 B1 | 11/2001 | Lewis et al. | |
| 6,485,500 B1 * | 11/2002 | Kokish et al. | 606/194 |
| 6,595,963 B1 | 7/2003 | Barbut | |
| 6,692,509 B2 | 2/2004 | Wensel et al. | |
| 7,093,527 B2 | 8/2006 | Rapaport et al. | |
| 7,318,815 B2 | 1/2008 | Qureshi et al. | |
| 7,691,121 B2 | 4/2010 | Rosenbluth et al. | |
| 7,955,344 B2 * | 6/2011 | Finitsis | 606/159 |
| 8,066,757 B2 | 11/2011 | Ferrera et al. | |
| 8,070,791 B2 | 12/2011 | Ferrera et al. | |
| 8,088,140 B2 | 1/2012 | Ferrera et al. | |
| 8,197,493 B2 | 6/2012 | Benjamin et al. | |
| 2001/0016726 A1 * | 8/2001 | Dubrul et al. | 604/509 |
| 2002/0010487 A1 * | 1/2002 | Evans et al. | 606/180 |
| 2002/0016624 A1 | 2/2002 | Patterson et al. | |
| 2002/0161392 A1 * | 10/2002 | Dubrul | 606/200 |
| 2003/0028238 A1 * | 2/2003 | Burkett et al. | 623/1.11 |
| 2003/0078605 A1 * | 4/2003 | Bashiri | A61B 17/221 606/159 |
| 2003/0208262 A1 * | 11/2003 | Gaber | 623/1.17 |
| 2004/0082962 A1 | 4/2004 | Demarais et al. | |
| 2004/0153119 A1 * | 8/2004 | Kusleika et al. | 606/200 |
| 2007/0208367 A1 | 9/2007 | Fiorella et al. | |
| 2008/0249458 A1 | 10/2008 | Yamasaki | |
| 2008/0262598 A1 | 10/2008 | Elmaleh | |
| 2009/0030499 A1 | 1/2009 | Bebb et al. | |
| 2009/0099640 A1 * | 4/2009 | Weng | A61F 2/95 623/1.11 |
| 2009/0105722 A1 | 4/2009 | Fulkerson et al. | |
| 2009/0105737 A1 * | 4/2009 | Fulkerson et al. | 606/159 |
| 2009/0125053 A1 | 5/2009 | Ferrera et al. | |
| 2009/0187240 A1 | 7/2009 | Clerc et al. | |
| 2009/0198269 A1 | 8/2009 | Hannes et al. | |
| 2009/0292307 A1 | 11/2009 | Razack | |
| 2009/0299393 A1 | 12/2009 | Martin et al. | |
| 2010/0087850 A1 | 4/2010 | Razack | |
| 2010/0114017 A1 | 5/2010 | Lenker et al. | |
| 2010/0114135 A1 | 5/2010 | Wilson et al. | |
| 2010/0160951 A1 * | 6/2010 | Madison | 606/198 |
| 2010/0174309 A1 | 7/2010 | Ferrera et al. | |
| 2010/0217187 A1 | 8/2010 | Fulkerson et al. | |
| 2010/0256600 A1 * | 10/2010 | Ferrera | 604/509 |
| 2010/0318097 A1 | 12/2010 | Ferrera et al. | |
| 2010/0318178 A1 | 12/2010 | Rapaport et al. | |
| 2011/0160757 A1 | 6/2011 | Benjamin et al. | |
| 2011/0160760 A1 | 6/2011 | Benjamin et al. | |
| 2011/0190797 A1 | 8/2011 | Ferrera et al. | |
| 2011/0213403 A1 | 9/2011 | Aboytes | |
| 2011/0238106 A1 | 9/2011 | Ferrera et al. | |
| 2011/0319917 A1 | 12/2011 | Ferrera et al. | |
| 2012/0016406 A1 | 1/2012 | Ferrera et al. | |
| 2012/0022576 A1 | 1/2012 | Ferrera et al. | |
| 2012/0041460 A1 | 2/2012 | Ferrera et al. | |
| 2012/0041475 A1 | 2/2012 | Ferrera et al. | |
| 2012/0065660 A1 | 3/2012 | Ferrera et al. | |
| 2012/0116443 A1 | 5/2012 | Ferrera et al. | |

FOREIGN PATENT DOCUMENTS

| | | |
|---|---|---|
| EP | 1915434 | 4/2008 |
| EP | 2 442 860 A1 | 4/2012 |
| WO | 2007089897 A2 | 8/2007 |
| WO | 2010/062363 A1 | 6/2010 |
| WO | WO 2010/146581 A1 | 12/2010 |

OTHER PUBLICATIONS

Reza Jahan, Abstract of "A Novel, Self Expanding, Fully Retrievable Flow Restoration Device for Treatment of Acute Ischemic Stroke", American Heart Association, Inc., Stroke ePosters Archives, downloaded on Mar. 21, 2009.

A. Staylor, et al., "Ischemic Stroke: Prying Open the Treatment Window", medtech insight, Apr. 2010, pp. cover, 36-51, vol. 12, No. 4, Published by Elsevier Business Intelligence.

R. G. Nogueira, et al., "Endovascular Approaches to Acute Stroke, Part 1: Drugs, Devices, and Data", American Journal of Neuroradiology, Apr. 2009, vol. 30, pp. 649-661.

R. G. Nogueira, et al., Endovascular Approaches to Acute Stroke, Part 2: A Comprehensive Review of Studies and Trials, Apr. 22, 2009, pp. 1-17.

International Search Report for parallel PCT application PCT/IL2010/000470, Issued by the European Patent Office, of Mailing Date Nov. 19, 2010.

Written Opinion for the International Search Report for parallel PCT application PCT/IL2010/000470, Issued by the European Patent Office, of Mailing Date Nov. 19, 2010.

Office Action for U.S. Appl. 12/815,428, of Mailing Date Mar. 2, 2012.

A. Staylor, "The Ongoing Evolution in Device-Based Stroke Intervention: An Interview with Adnan Siddiqui", medtech insight, Apr. 2010, pp. 52-55, vol. 12, No. 4, Published by Elsevier Business Intelligence.

Advisory Action Before the Filing of an Appeal Brief Dated Mar. 29, 2013 From the US Patent and Trademark Office Re. U.S. Appl. No. 12/815,428.

(56) References Cited

OTHER PUBLICATIONS

Official Action Dated Mar. 2, 2012 From the US Patent and Trademark Office Re. U.S. Appl. No. 12/815,428.
Barreto, et al., "Thrombus Burden Is Associated With Clinical Outcome After Intra-Arterial Therapy for Acute Ischemic Stroke", Stroke Journal of the American Heart Association, Sep. 2008, pp. 3231-3235.
Cassels, "Thromboembolic Clots Have Same Composition Regardless of Source", Medscape Medical News, Aug. 2006, 3 pages.
Marder, et al., "Analysis of Thrombi Retrieved From Cerebral Arteries of Patients With Acute Ischemic Stroke", Stroke Journal of the American Heart Association, Jun. 2006, pp. 2086-2093.
First Office Action for corresponding European Patent Application No. 10737635.2 dated May 13, 2013, 5 pages.
Final Office Action for U.S. Appl. No. 12/815,428 mailed on Oct. 12, 2012, 17 pages.
International Preliminary Report on Patentability Dated Dec. 29, 2011 From the International Bureau of WIPO Re. Application No. PCT/IL2010/000470.
Official Action Dated Jul. 31, 2014 From the US Patent and Trademark Office Re. U.S. Appl. No. 12/815,428.
Official Action Dated Jan. 26, 2015 From the US Patent and Trademark Office Re. U.S. Appl. No. 12/815,428.
Communication Pursuant to Article 94(3) EPC Dated Apr. 30, 2015 From the European Patent Office Re. Application No. 10737635.2.
Official Action Dated May 20, 2015 From the US Patent and Trademark Office Re. U.S. Appl. No. 12/815,428.

\* cited by examiner

METHOD AND APPARATUS FOR ALLOWING BLOOD FLOW THROUGH AN OCCLUDED VESSEL

BACKGROUND OF THE INVENTION

The invention relates generally to the field of medical devices, specifically to medical devices that are useful in treating stroke, and more particularly to a device allowing for the flow of oxygenated blood through an obstructed artery thus sustaining at least partial patency.

Stroke is a leading cause of disability, death and health care expenditure. Most strokes are ischemic, i.e. caused by a decrease in the blood supply to a portion of the brain due to a clot obstructing the flow of blood. A total or hemodynamically significant occlusion of a cerebral artery in an acute ischemic stroke is mostly due to thrombus formation, an embolus, and/or other unwanted matter. When an artery is obstructed, tissue ischemia (lack of oxygen and nutrients) quickly develops. The organ most sensitive to ischemia is the brain. Ischemia will rapidly progress to tissue infarction (cell death) if the occlusion of blood flow persists. In patients experiencing a typical large vessel acute ischemic stroke, it has been estimated that within each hour of no cerebral perfusion, about 20 million neurons are lost. Therefore, cerebral artery occlusions that lead to stroke require swift and effective therapy to reduce the morbidity associated with the disease. The term occlusion as used herein is meant to include any partial or complete blockage of a blood vessel, as by thrombosis, embolism or gradual narrowing.

The functionally impaired region that surrounds the infarct core and is threatened by cell death has been termed the ischemic penumbra. The ischemic penumbra, although physiologically impaired, is potentially salvageable tissue, however the window of opportunity for recovery of the reversibly injured neurons in the ischemic penumbra is relatively short. Failure to timely restore blood flow triggers a biochemical and metabolic cascade ultimately leading to irreversible brain injury by progressive transformation of the ischemic penumbra into infarcted tissue, i.e. the infarct core expands as the penumbra tissue experiences necrosis.

Traditionally, emergency management of acute ischemic stroke consisted of mainly general supportive care, e.g. hydration, monitoring neurological status, blood pressure control, and/or anti-platelet or anti-coagulation therapy. In 1996 intra-arterial administration of tissue plasminogen activator (t-PA) was approved by the FDA for the treatment of acute ischemic stroke in selected cases within the first few hours from onset. More recently percutaneous catheter-based technologies have been advanced, including: placing a microcatheter near the clot and infusing a thrombolytic agent in order to dissolve the clot; extracting the clot by distal embolectomy devices in which various wire corkscrews and baskets are advanced distally through the clot in order to capture it; and using proximal devices in which the clot is aspirated or captured and removed. Other methods of removing or disrupting the clot, include: facilitating fibrinolysis by an outside energy source such as ultrasound or laser energy; mechanical manipulation of the clot by primary angioplasty; and employing stents permanently or transiently are also widely used.

Often, more than one method is required until arterial patency is restored. Such treatment approaches have a common purpose of restoring artery patency as quickly as possible by removing or disrupting the obstructing clot. Achieving artery patency by any of these above methods or any combination of them (multimodal therapy) is often complex, requires multiple steps and is time consuming. Even if the treatment is successful, during the treatment progressive transformation of the penumbra into infarcted tissue occurs.

A key therapeutic goal of acute ischemic stroke treatment consists of re-establishment of arterial potency prior to cell death. The sooner arterial patency is achieved the greater the clinical benefit, therefore early restoration of blood flow in the affected territory of the brain may save brain tissue.

Cells within an infarction zone have dramatically reduced blood flow to less than 20% of normal blood flow. As a result, cells within this infarction zone will be irreversibly damaged within a few minutes. The blood flow in the ischemic penumbra, surrounding the infarction zone, is between 20% and 50% of normal. Cells in this area are endangered, but not irreversibly damaged. Studies have indicated that a critical focal stenosis of ~75% decrease in diameter is usually required to compromise flow in a major cerebral artery, in face of insufficient collateral flow from other arteries.

U.S. Patent Application Publication S/N 2007/0208367 published Sep. 6, 2007 to Fiorella et al is directed to a method of increasing blood flow through an obstructed blood vessel includes providing an expandable member substantially made of a mesh having a plurality of interstices. The expandable member is expanded to bring at least a portion of the member body into contact with the occlusion. An outward radial force is exerted on the occlusion to dislodge at least one fragment from the occlusion and to enhance blood flow through the blood vessel past the occlusion. Disadvantageously, the radial force required may traumatize the blood vessel exhibiting the occlusion. A means for capturing the dislodged fragment is provided, however the blood flow interruption due to the capturing mesh itself induces flow resistance. Additionally, aggregation of the dislodged fragments in the capturing mesh disrupts and subsequently decreases the blood flow.

U.S. Pat. No. 6,295,990 issued Oct. 2, 2001 to Lewis et al, the entire contents of which is incorporated herein by reference, is addressed to methods for treating total and partial occlusions by employing a perfusion conduit which is penetrated through the occlusive material. Oxygenated blood or other medium is then perfused through the conduit in a controlled manner, preferably at a controlled pressure below the arterial pressure, to maintain oxygenation and relieve ischemia in tissue distal to the occlusion. The device and method of Lewis is based on an elongated solid catheter extending from outside the patient body until penetrating the occlusion. In an embodiment in which passive perfusion is implemented, blood inlet ports are provided near the proximal end with blood outlet ports provided at the distal end. The requirement for inlet and outlet ports fails to take full advantage of the pressure differential between the proximal and distal sides of the occlusion.

An article by Kelly et al published in Stroke, June 2008 at pages 39: 1770-1773 entitled "Recanalization of an Acute Middle Cerebral Artery Occlusion Using a Self-Expanding, Reconstrainable, Intracranial Microstent as a Temporary Endovascular Bypass is addressed to providing a temporary bypass using a self expanding stent. Disadvantageously, the self expanding stent exerts radial force against the occlusion, which may result in undesired breaking up of the occlusion with significant fragments being dislodged to proceed further into the bloodstream resulting in potential brain damage.

There is thus a need for a method and apparatus for passively perfusing oxygenated blood through an obstructing clot while minimizing undesired radial force against the occlusion.

SUMMARY OF THE INVENTION

In view of the discussion provided above and other considerations, the present disclosure provides methods and apparatuses for sustaining patency through an occlusion. This is accomplished in certain embodiments by providing a device arranged to provide and/or sustain at least partial patency of a small blood vessel exhibiting an occlusion. The device comprises a tubular body expandable from an initial small diameter state for manipulation adjacent, and/or through, the occlusion of the small blood vessel and a second large diameter state. In some embodiments, the second large diameter is limited to a maximal allowed value, thus preventing undesired radial force against the occlusion. Optionally, the second large diameter state is no more than 50% of the diameter of the blood vessel at the occlusion location. The term small blood vessel as used herein is defined as a blood vessel of 5 mm or less of inner diameter and may be constituted of an intracranial blood vessel.

In one embodiment the device is a self expanding device. In one embodiment the device in its large diameter state is of a generally circular shape. In one embodiment the device is an expanded collapsible conduit between 2 and 40 millimeters longer than the maximal length of the occlusion.

Certain embodiments provide for a device arranged to sustain at least partial patency of a small blood vessel exhibiting an occlusion, the device comprising a tubular body exhibiting a first small diameter state for manipulation to, and through, the occlusion of the small blood vessel, the device expandable to a second large diameter state within the occlusion, the inner dimensions of the second large diameter state being no more than 50% of the diameter of the small blood vessel at the occlusion location, the device presenting a conduit through the tubular body for blood flow through the occlusion when in the large diameter state.

In some embodiments the tubular body in the second large diameter state does not urge to expand beyond 50% of the diameter of the small blood vessel. In some embodiments the tubular body in the second large diameter state exhibits a length at least 14 times the inner diameter of the tubular body in the second large diameter state.

In some embodiments the tubular body in the second large diameter state exhibits an inner diameter no more than twice the inner diameter of the tubular body in the first small diameter state. In some embodiments the device further comprises a distal filtering extension coupled to a first end of the tubular body. In certain further embodiments the distal filtering extension is arranged to expand to meet the inner wall of the small blood vessel distal of the occlusion. In certain further embodiments the device further comprises a proximal securing member coupled to a second end of the tubular body, opposing the first end, the second securing portion arranged to expand to meet the inner wall of the small blood vessel.

In some embodiments the device further comprises a retraction mechanism arranged to collapse the device from the second large diameter state within the occlusion, wherein the device may be withdrawn. In some embodiments the device is coated with an elastic non-porous material.

In some embodiments the device is constituted of self expanding braided filaments. In some embodiment the device further comprises further comprising a clot retrieval device arranged to retrieve at least a portion of the occlusion, the clot retrieval device in communication with the tubular body and exhibiting a diameter greater than 50% of the diameter of the small blood vessel at the occlusion location.

In some embodiments the tubular body is coated with an elastic porous material. In some embodiments the small blood vessel is an intracranial blood vessel.

Independently certain embodiments provide for a temporary endovascular conduit system arranged to sustain partial patency of a small blood vessel exhibiting an occlusion, the temporary endovascular conduit system comprising: a catheter exhibiting an inside diameter; a device comprising a tubular body exhibiting a first small diameter state exhibiting an inner diameter less than the catheter inside diameter, the device expandable to a second large diameter state when the device is within the occlusion, the inner diameter of the second large diameter state being no more than 50% of the diameter of the small blood vessel at the occlusion location, the device presenting a conduit through the tubular body for blood flow through the occlusion when in the second large diameter state.

In some embodiments the tubular body in the second large diameter state does not urge to expand beyond 50% of the diameter of the small blood vessel at the occlusion location. In some embodiments the tubular body in the second large diameter state exhibits a length at least 14 times the inner diameter of the tubular body in the second large diameter state.

In some embodiments the tubular body in the second large diameter state exhibits an inner diameter no more than twice the inner diameter of the tubular body in the first small diameter state. In some embodiments the device further comprises a distal filtering extension member coupled to a first end of the tubular body. In certain further embodiments the distal filtering extension member is arranged to expand to meet the inner wall of the small blood vessel distal of the occlusion. In certain further embodiments the temporary endovascular conduit system further comprises a proximal securing member coupled to a second end of the tubular body, opposing the first end, the proximal securing member arranged to expand to meet the inner wall of the small blood vessel.

In some embodiments the temporary endovascular conduit system further comprises a pair of members in communication with the device, the device collapsible from the second large diameter state to the first small diameter state responsive to respective motion of the members. In some embodiments the tubular body is coated with an elastic non-porous material.

In some embodiments the tubular body is coated with an elastic porous material. In some embodiments the device is constituted of self expanding braided filaments. In some embodiments the temporary endovascular conduit system further comprises a clot retrieval device arranged to retrieve at least a portion of the occlusion, the clot retrieval device in communication with the tubular body and exhibiting a diameter greater than 50% of the diameter of the small blood vessel at the occlusion location.

In some embodiments the small blood vessel is an intracranial blood vessel. In some embodiments the temporary endovascular conduit system further comprises a member in communication with the device, the device collapsible from the second large diameter state to the first small diameter state responsive to pulling of the member.

Independently a system for restoring partial patency to a small blood vessel having an inner diameter and an occlusion is provided, the system comprising: a delivery catheter including a shaft having a shaft diameter and a recess adjacent a distal end of the shaft; and a hollow meshed tube deliverable into the small blood vessel and across the occlusion by the delivery catheter when retained in the recess and expandable from a first small diameter that is substantially similar to or less than the shaft diameter to a second large diameter that is substantially smaller than the Small blood vessel diameter; wherein the hollow mesh tube is selectively expandable to the second large diameter in the occlusion thereby disassociated from the recess and deployed to sustain a dimension of a passage traveling through the clogged portion previously created by the delivery catheter.

In some embodiments the second large diameter is no more than 200% of the first small diameter. In some embodiments the second larger diameter is no more than 50% of the small blood vessel diameter at the occlusion.

Independently a method of providing blood flow through a target small blood vessel exhibiting an occlusion is provided, the method comprising: selecting an expandable tubular body exhibiting a first small diameter state and a second large diameter state, the inner dimensions of the second large diameter state being no more than 50% of the diameter of the target blood vessel at the occlusion; advancing the selected expandable tubular body while in the first small diameter state through the occlusion; and expanding the selected and advanced expandable tubular body towards the second large diameter state thereby providing a conduit for blood flow through the occlusion, thereby allowing blood to flow through the selected expanded tubular body.

In some embodiments the selected expandable tubular body in the second large diameter state does not urge to expand beyond 50% of the diameter of the target small blood vessel at the occlusion. In some embodiments the method further comprises: selecting the expandable tubular body such that the further selected expandable tubular body in the second large diameter state exhibits a length at least 14 times the inner diameter of the expandable tubular body in the second large diameter state. In some embodiments the selected expandable tubular body in the second large diameter state exhibits an inner diameter no more than twice the inner diameter of the tubular body in the first small diameter state.

In some embodiments the selected expandable tubular body further comprises a distal filtering extension coupled to a distal end of the selected expandable tubular body. In some further embodiments the method comprises expanding the distal filtering extension to meet the inner wall of the target blood vessel distal of the occlusion. In some further embodiment the selected expandable tubular body further comprises a proximal securing member coupled to a proximal end of the selected expandable tubular body, the method further comprising expanding the proximal securing member to meet the inner wall of the target small blood vessel proximal of the occlusion.

In some embodiments the method further comprises: contracting the selected expanded tubular body from the second large diameter state within the occlusion; and withdrawing the contracted selected tubular body from the target small blood vessel. In some further embodiments the contracting is to the first small diameter state.

In some embodiments the method further comprises delivering a medicament to the occlusion through the selected expanded tubular body. In some embodiments the method further comprises withdrawing at least a portion of the occlusion from the target blood vessel.

Independently a method of providing blood flow through a target small blood vessel exhibiting an occlusion is provided, the method comprising: providing an expandable tubular body exhibiting a first small diameter state and a second large diameter state, the inner dimensions of the second large diameter state being no more than 50% of the diameter of the target small blood vessel at the occlusion; advancing the provided expandable tubular body while in the first small diameter state through the occlusion; and expanding the provided and advanced expandable tubular body towards the second large diameter state thereby creating a conduit for blood flow through the occlusion, the conduit constituted of the provided expanded tubular body.

In some embodiments the provided expandable tubular body in the second large diameter state does not urge to expand beyond 50% of the diameter of the target blood vessel at the occlusion. In some embodiments the provided expandable tubular body in the second large diameter state exhibits a length at least 14 times the inner diameter of the expandable tubular body in the second large diameter state. In some embodiments the provided expandable tubular body in the second large diameter state exhibits an inner diameter no more than twice the inner diameter of the tubular body in the first small diameter state.

In some embodiments the provided expandable tubular body further comprises a distal filtering extension coupled to a distal end of the selected expandable tubular body. In some further embodiments the method further comprises expanding the distal filtering extension to meet the inner wall of the target small blood vessel distal of the occlusion. In some further embodiments the provided expandable tubular body further comprises a proximal securing member coupled to a proximal end of the selected expandable tubular body, the method further comprising expanding the proximal securing member to meet the inner wall of the target small blood vessel proximal of the occlusion.

In some embodiments the method further comprises: contracting the provided expanded tubular body from the second large diameter state within the occlusion; and withdrawing the contracted provided tubular body from the target small blood vessel. In some embodiments the contracting is to the first small diameter state. In some embodiments the method further comprises delivering a medicament to the occlusion through the provided expanded tubular body. In some embodiments the method further comprises withdrawing at least a portion of the occlusion from the target small blood vessel.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
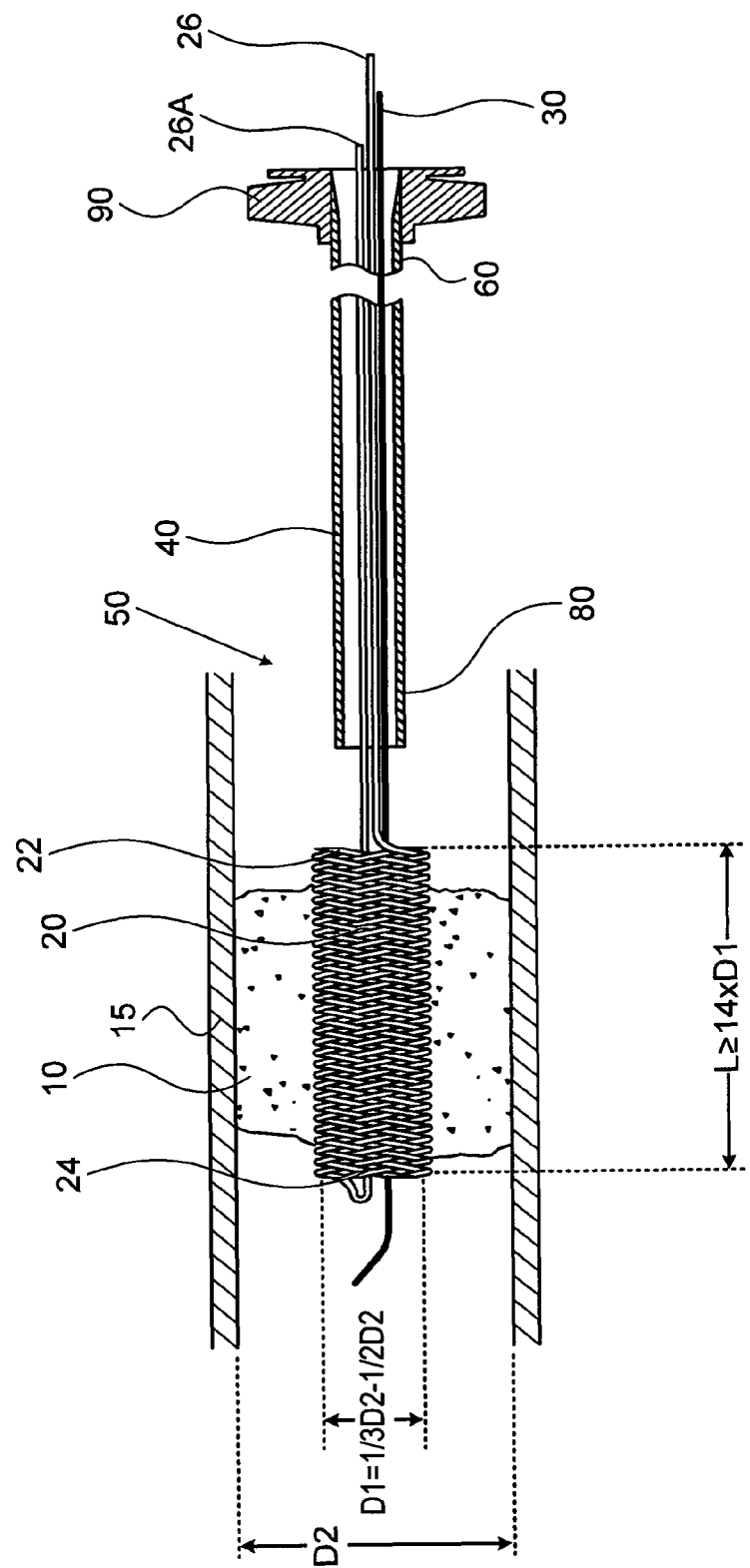
FIG. 1 illustrates a high level schematic diagram of a sectioned view of a first embodiment of a temporary endovascular conduit system, comprising a self expanding device.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a high level schematic diagram of a sectioned view of a first embodiment of a temporary endovascular conduit system, denoted temporary endovascular conduit system 50, deployed in an occlusion 10 occluding a body lumen 15. Temporary endovascular conduit system 50 comprises: a catheter 40, exhibiting a proximal portion 60 and a distal portion 80; a hub 90; a pair of members 26 and 26A; a guide wire 30; and a self expanding device 20, exhibiting a proximal end 22 and a distal end 24, illustrated in a large diameter state. The diameter of body lumen 15 in the area of occlusion 10 is denoted D2, and the inner diameter of self expanding device 20 in the large diameter state, denoted D1, is preferably between ⅓ and ½ of D2. Body lumen 15 is a small blood vessel, exhibiting an inner diameter D2 of 5 mm or less, as described above. Advantageously, providing a conduit exhibiting an inner diameter for blood flow of at least ⅓ of D2 allows a sufficient blood flow, in the absence of sufficient collateral flow from other arteries, to prevent or delay cell death, since this provides for a resultant stenosis of less than 75%.

Proximal end 22 of self expanding device 20 is positioned proximally to occlusion 10 and distal end 24 of self expanding device 20 is positioned distally to occlusion 10. Self expanding device 20 in the large diameter state provides a conduit for limited blood flow from proximal end 22 to distal end 24. In one non-limiting embodiment the length of self expanding device 20 in the large diameter, denoted L, is at least 5 times D1. In another non-limiting embodiment length L is at least 10 times D1. In another non-limiting embodiment length L is at least 15 times D1. In another non-limiting embodiment length L is at least 20 times D1. In another non-limiting embodiment length L is at least 30 times D1. In one particular non-limiting embodiment length L is at least 14 times D1. Thus, a conduit of sufficient length to extend from a point proximal of occlusion 10 to a point distal of occlusion 10 is provided. Hub 90 is attached to proximal portion 60 of catheter 40. In one embodiment members 26 and 26A are respectively connected to proximal end 22 and distal end 24 of self expanding device 20. Members 26, 26A and guide wire 30 run through catheter 40 and hub 90 and out therefrom, and are provided to be long enough so as to be accessible.

The structure of self expanding device 20 can be of any kind, provided it is hollow, including, but not limited to, a tubular tube, a shield tube and a self expanding structure manufactured by any one of weaving, coiling, laser cutting and braiding a plurality of filaments. Optionally, self expanding device 20 is a self expandable braided tubular member, as illustrated. The braid construction that forms self expanding device 20 can be produced from many different materials, including, but not limited to, metals, polymers and composites. More specifically, these materials can include cobalt-chrome alloys, stainless steel, nylon, and polyesters. In one embodiment, superelastic materials such as some nickel titanium alloys, are used. In one particular embodiment a formulation of nickel titanium alloy comprising about 51%-56% nickel and about 44%-49% titanium is used.

Figure 2A:
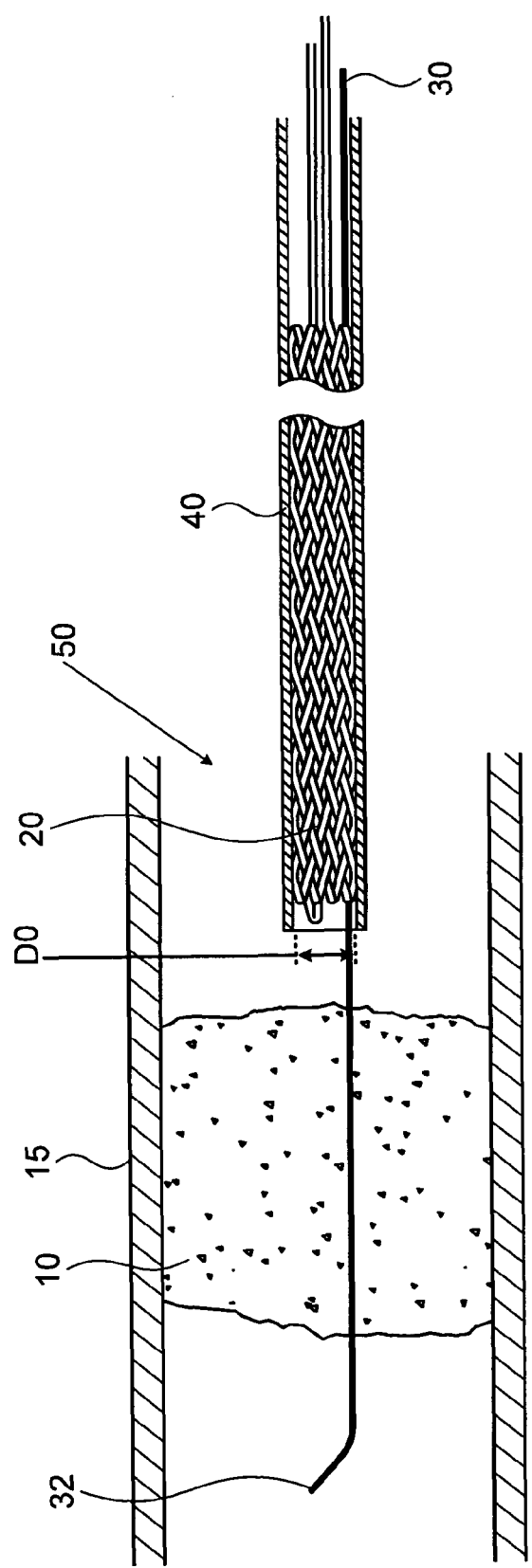
FIGS. 2A-2E illustrate high level schematic diagrams of partially sectioned views of the distal portion of the temporary endovascular perfusion conduit system of FIG. 1, showing sequential steps in the deployment of the self expanding device in a vessel according to an exemplary embodiment.

In one embodiment each filament comprising self expanding device 20 has a round cross section, the diameter of the cross section usually ranging between about 0.0005 inches and 0.01 inches and optionally between 0.001 inches and 0.004 inches, and the number of filaments comprising the braided construction ranges between 4 and 288. In another embodiment the filaments comprising self expanding device 20 are flat wires with non-circular cross sections, the number of filaments ranging between 8 and 64, optionally between 12 and 24. In one embodiment the braiding angle is between 60° and 150°. In one particular embodiment the braiding angle is 90°. In one embodiment the braiding pattern is a regular pattern known also as herringbone or 1×2 pattern. In another embodiment a braiding pattern of 1×1 is used, with such a braiding pattern also known as a "one over one under" pattern. In one embodiment self expanding device 20 is permeable to fluids. The inner diameter of self expanding device 20 is in the first small diameter state, denoted D0, when self expanding device 20 is held within catheter 40 as illustrated in FIG. 2A described further below. In some embodiments D0 is between 0.5 mm and 1.5 mm, optionally between 0.8 mm and 1.2 mm and diameter D1 is between 0.8 mm and 2 mm, optionally between 1 mm and 1.5 mm. In certain embodiments the length of self expanding device 20 stays fixed when the diameter of self expanding device 20 changes, and in other embodiments, the length of self expanding device 20 is reduced when the inner diameter of self expanding device 20 increases. Alternatively, self expanding device 20 is substantially not expanded or only slightly expands when elongated to length L.

Figure 3:
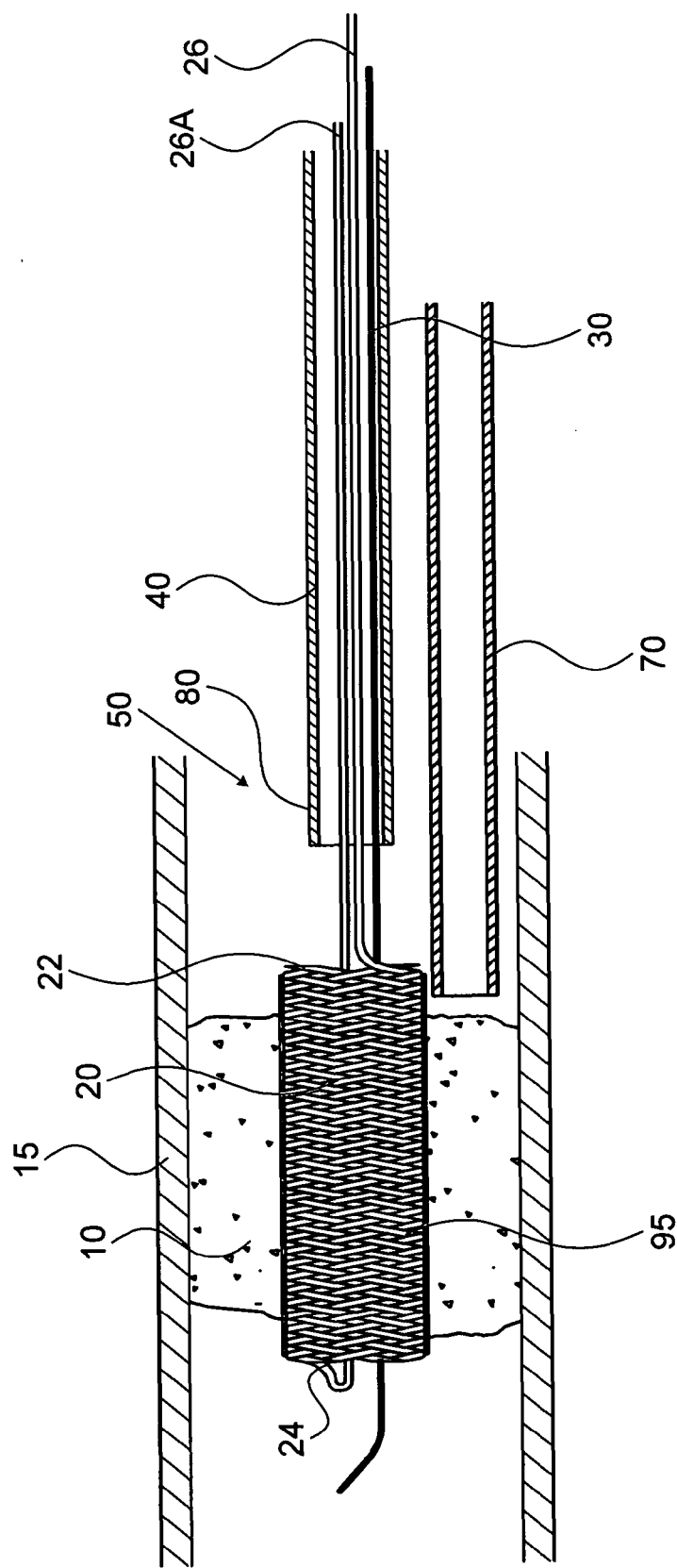
FIG. 3 illustrates a high level schematic diagram of a partially sectioned view of the distal portion of the temporary endovascular perfusion conduit system of FIG. 1 and a delivery mechanism for intra-arterial administration of a medicament according to an exemplary embodiment.

In one embodiment the braid construction that forms self expanding device 20 is coated with a non-porous elastic material, illustrated in FIG. 3 as a coating 95. Coating over the porous braid construction of self expanding device 20 forms a solid tubular conduit within occlusion 10. The elastic material can be any of a plurality of materials, including, but not limited to: polymers such as silicones, polyethers, polyurethanes, polyamides, hydrogels such as polyvinyl alcohol or polyvinyl pyrrolidone, and other polymers suitable for intravascular use; permeable, semi-permeable and non-permeable membranes; and expandable foams. The elastic material is preferably formed into a fabric mesh and placed around self expanding device 20. Optionally, the elastic material is porous, preferably less permeable than self expanding device 20.

In the absence of a non-porous elastic material coating, any particles from occlusion 10 which pass through the relatively small openings forming self expanding device 20 flow out therefrom, thereby avoiding harmful disruption of blood flow or occlusion of a vessel thereof.

Self expanding device 20 in the large diameter state, as shown, provides and/or sustains a conduit exhibiting an minimum inner diameter D1 for sufficient blood flow to the region distal of occlusion 10 and from there to the affected area, thereby reducing the infarction rate of penumbral tissue. As a result, the effective time window for performing endovascular attempts to remove or disrupt occlusion 10 is expanded. Shortening the length and/or increasing the hollow cross-section diameter of self expanding device 20 may result in greater cerebral blood flow to the region distal to occlusion 10 and from there to the affected area, resulting in a greater reduction in the infarction rate of penumbral tissue. In one embodiment length L of self expanding device 20 in a maximum expanded state is provided to be as short as possible, while being longer than the length of occlusion 10, optionally between 2 mm and 40 mm longer than the length of occlusion 10, and the diameter of the hollow cross-section of self expanding device 20 in a maximum expanded state is provided to be between ⅓ and ½ of diameter D2 of body lumen 15, as described above. In one embodiment, where occlusion 10 is 10 mm long, length L is 20 mm, thereby extending 5 mm proximally of occlusion 10 and 5 mm distally of occlusion 10. In another embodiment, where occlusion 10 is 20-30 mm long, length L between 40 mm and 50 mm, thereby extending between 5 mm and 15 mm proximally of occlusion 10 and between 5 mm and 15 mm distally of occlusion 10. Self expanding device 20 provides enough radial force at diameters up to the unstressed maximum expanded state of ½ of D2 so as to prevent movement of self expanding device 20 in occlusion 10, while being small enough so as not traumatize the walls of body lumen 15. In one non-limiting embodiment, the inside diameter of self expanding device 20 in its maximum expanded state represents a conduit with a cross section of at least 0.685 mm$^2$. When self expanding device 20 is at its maximum expanded state it is considered to be at its resting state, since no radial expansion force is exhibited by self expanding device 20, in particular self expanding device 20 does not urge to expand beyond said second large diameter state. Thus, self expanding device 20 may exhibit outward radial force when within occlusion 10, until expansion has reached the unstressed maximum expanded state of ½ of D2. Once self expanding device 20 has reached the unstressed maximum expanded state of ½ of D2 no radial force is applied to occlusion 10. Furthermore no radial force is applied to the walls of body lumen 15 distally and proximally of occlusion 10.

Members 26, 26A are provided in order to facilitate the deployment of self expanding device 20 into occlusion 10, particularly aiding in control of localization and further procedures, and/or the ultimate retraction of self expanding device 20 therefrom. Members 26 and 26A are in one embodiment each constituted of one of a flexible rod, a filament or a bundle of filaments. In one embodiment the cross section of each of members 26 and 26A are on the same order as the cross section of guidewire 30, with guidewire 30 preferably being a 0.014" (0.3556 mm) guidewire known to the art exhibiting a cross-sectional area of less than 0.1 mm$^2$. In the embodiment in which member 26 is connected to proximal end 22 of self expanding device 20 and member 26A is connected to distal end 24 of self expanding device 20, stretching and compressing of self expanding device 20 is enabled by respectively relatively pulling and pushing members 26 and 26A to expand and decrease the length between proximal end 22 and distal end 24. Stretching self expanding device 20 reduces its cross-sectional area and enables an operator to change the placement of self expanding device 20 easily. Compressing self expanding device 20 enlarges its hollow cross-sectional area so as to allow more blood flow there through, as described above. As will be described below in relation to FIG. 2D, self expanding device 20 can be retracted into catheter 40 by pulling member 26 or by pulling and pushing members 26, 26A, respectively, and withdrawn from the patient body along with the retraction of catheter 40.

In another embodiment members 26,26A are inherently connected to self expanding device 20, i.e. members 26,26A are thin local elongated protrusions of self expanding device 20. There is no requirement that a single catheter 40 be provided for both delivery of self expanding device 20 and withdrawal of self expanding device 20. In one embodiment, withdrawal of self expanding device 20 comprises reduction in radial size to a size greater than the radial size of self expanding device when first delivered to occlusion 10.

In order to enable visualization of the construction that forms self expanding device 20 under fluoroscopy, in one embodiment numerous radiopaque materials such as gold, platinum, or tungsten can be applied using various methods such as marker, electroplating, ion deposition, and coating. In some embodiments, self expanding device 20 is at least partially coated with a radiopaque polymer such as silicone mixed with tantalum powder thus providing visualization.

Optionally, self expanding device 20 is secured in location within occlusion 10 by catheter 40 or by another anchoring means secured externally of the patient body, such as by members 26, 26A and 26B, to be described further below.

FIGS. 2A-2E illustrate high level schematic diagrams of partially sectioned views of the distal portion of temporary endovascular conduit system 50 of FIG. 1, showing sequential steps in the deployment of self expanding device 20 within body lumen 15 across occlusion 10 according to an exemplary embodiment, the description of FIGS. 2A-2E being taken together. In FIG. 2A self expanding device 20 is in a collapsed state, i.e. a small diameter state, and secured within catheter 40, and particulary in a distal portion of catheter 40. Self expanding device 20 is pre-loaded or back-loaded onto guidewire 30 while secured within catheter 40. Guidewire 30 is manipulated through body lumen 15 from an entry site, such as the femoral artery, to the region of body lumen 15 occluded by occlusion 10. A distal tip 32 of guidewire 30 is advanced across occlusion 10 using appropriate guidewire and crossing techniques known in the art. Once distal tip 32 of guidewire 30 passes through the distal end of occlusion 10, catheter 40 is advanced through occlusion 10. In one embodiment, after distal tip 32 of guidewire 30 has passed through the distal end of occlusion 10, a micro catheter can be used to visualize the patency of both the vasculature proximal to occlusion 10 and the vasculature distal to occlusion 10 using conventional radiographic techniques, prior to advancing catheter 40 over guidewire 30.

Figure 2B:
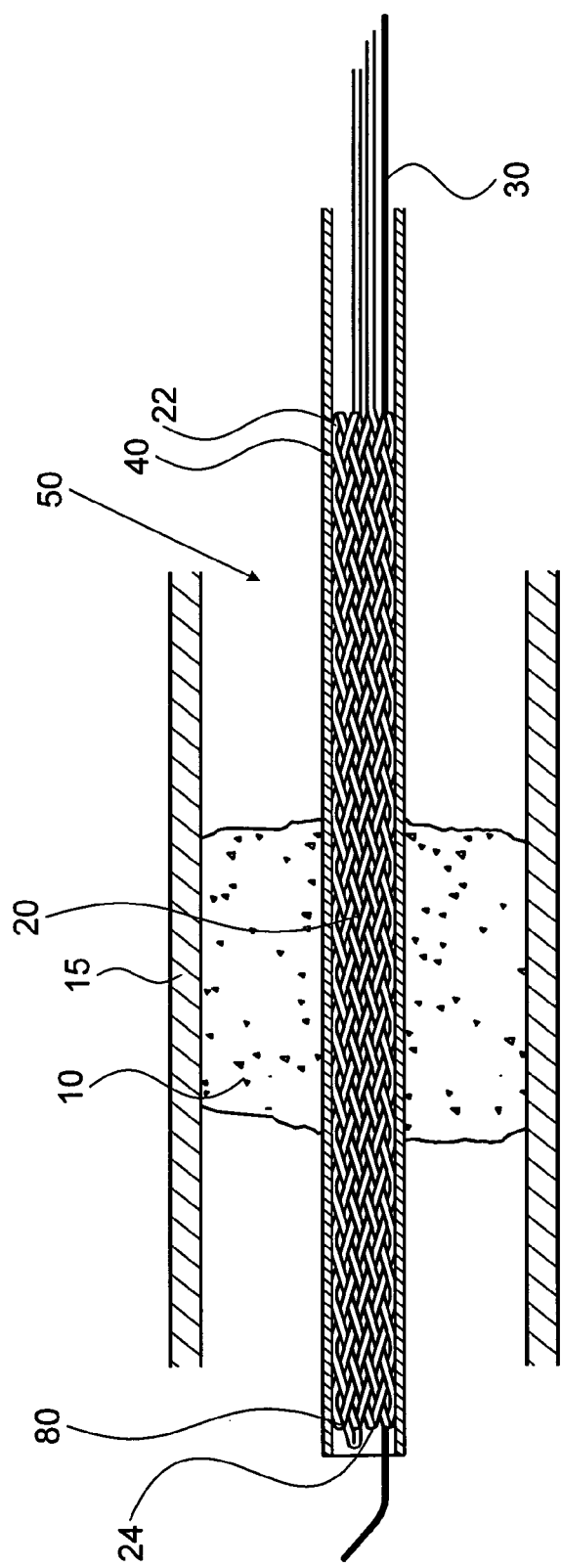

In FIG. 2B temporary endovascular conduit system 50 comprising catheter 40 constraining self expanding device 20 is advanced through occlusion 10, with distal portion 80 of catheter 40 and distal end 24 of self expanding device 20 extending distally of occlusion 10. In one embodiment, a radiographic solution may be injected through hub 90 of FIG. 1 prior to advancing temporary endovascular conduit system 50 into occlusion 10, thus after the positioning of catheter 40 across occlusion 10 the length of occlusion 10 can be determined, thereby allowing an operator to determine the desired positions of distal end 24 and proximal end 22 of self expanding device 20. In another embodiment, determining of the length of occlusion 10 is performed prior to inserting temporary endovascular conduit system 50 in the patient body, thus enabling the operator to choose a specific self expanding device 20 with desired final length and expanded large diameter. Various methods can be applied to visualize proximal end 22 and distal end 24 of self expanding device 20 under fluoroscopy, as described above in relation to FIG. 1.

Figure 2C:
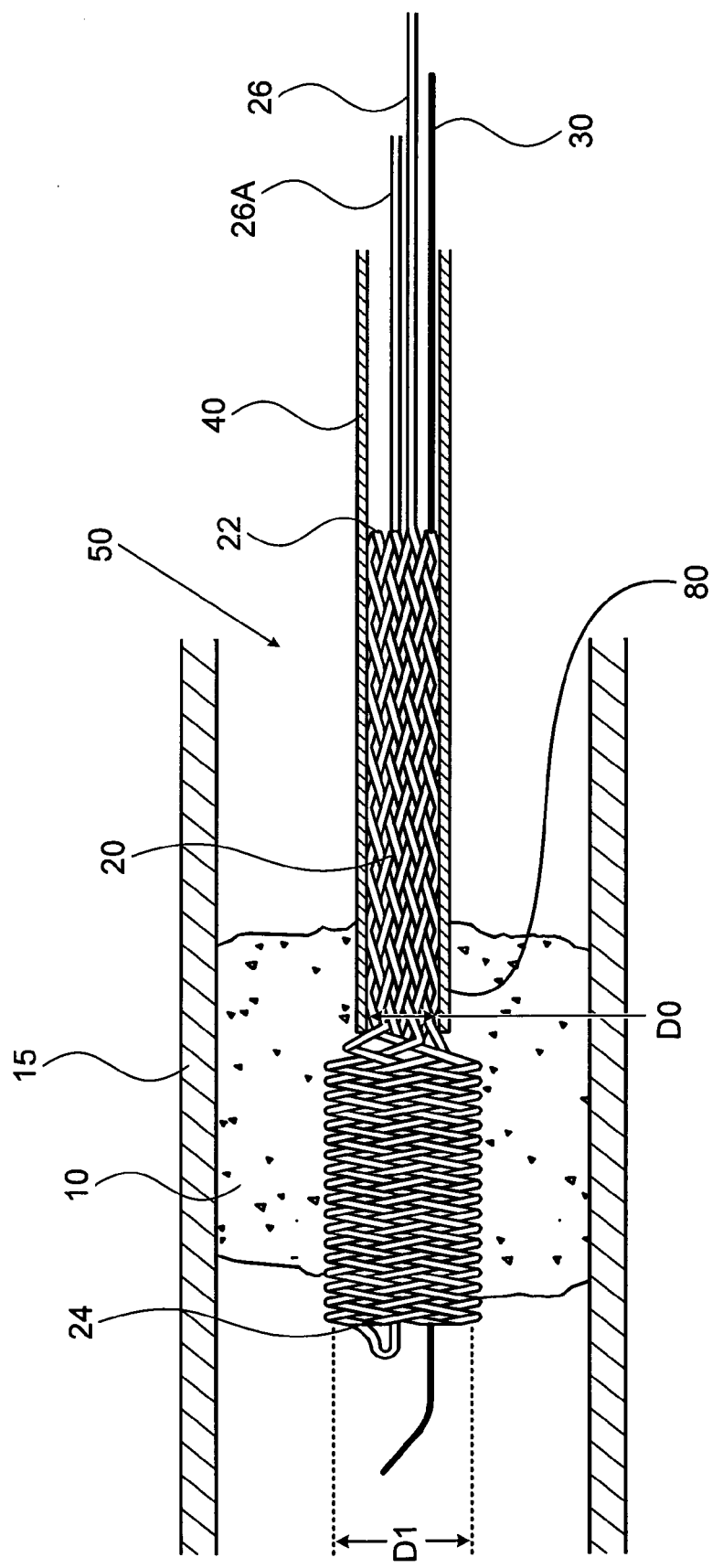

In FIG. 2C catheter 40 is partially retracted from restraining self expanding device 20, while members 26, 26A are held in place, thereby partially releasing self expanding device 20 from catheter 40 through distal portion 80. Due to self expanding properties the exposed part of self expanding device 20 automatically performs an outward radial expansion and preferably forms into a generally circular configuration. Optionally, inner diameter D1 of self expanding device 20 in the large diameter state is no greater than twice, optionally no greater than 1.5 times, and further optionally no greater than 1.2 times the inner diameter D0 of self expanding device 20 in the first small diameter state when held within catheter 40.

Figure 2D:
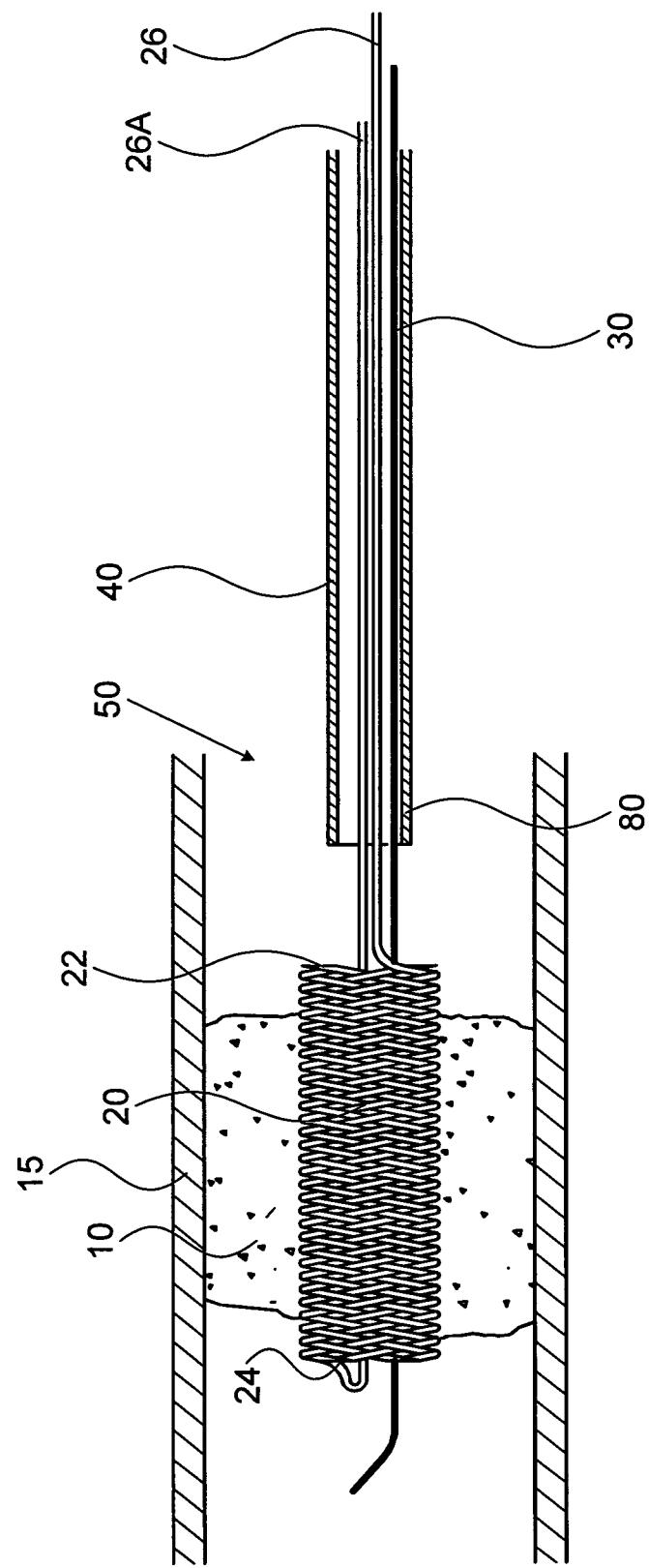

In FIG. 2D catheter 40 is retracted until self expanding device 20 is fully released. Self expanding device 20 expands to its large diameter state, presenting a conduit for blood flow through occlusion 10. Catheter 40 may be fully retracted from the patient body. In one embodiment guidewire 30 remains positioned in occlusion 10 to provide guidance for maneuvering medical means to the site of occlusion 10. In another embodiment guidewire 30 is removed from the patient body and member 26 and/or member 26A provides guidance for maneuvering medical means to the site of occlusion 10, thus enabling extended medical procedures without the need of guidewire 30.

Temporary endovascular conduit system 50 can be fully retracted out of the patient body, whenever necessary. In one embodiment this is accomplished by expanding the length of self expanding device 20 by manipulation of members 26, 26A thereby reducing the diameter of self expanding device 20. Once the diameter of self expanding device 20 has been reduced, catheter 40 is preferably advanced over self expanding device 20 while self expanding device 20 is held in the small diameter state by members 26, 26A, and catheter 40 containing therein self expanding device 20 is then removed from the patient body. Alternatively, catheter 40 is held stationary and self expanding device 20 in the small diameter state is withdrawn from the area of occlusion 10 towards distal portion 80 of catheter 40, and then drawn within catheter 40. In an alternative embodiment, self expanding device 20 is maintained in the small diameter state by the manipulation of members 26, 26A and removed from the patient body by further manipulation of members 26, 26A.

Advantageously, since self expanding device 20 may be collapsed and returned within catheter 40, numerous deployments of self expanding device 20 at various locations may be performed as a single endovascular procedure.

Figure 2E:
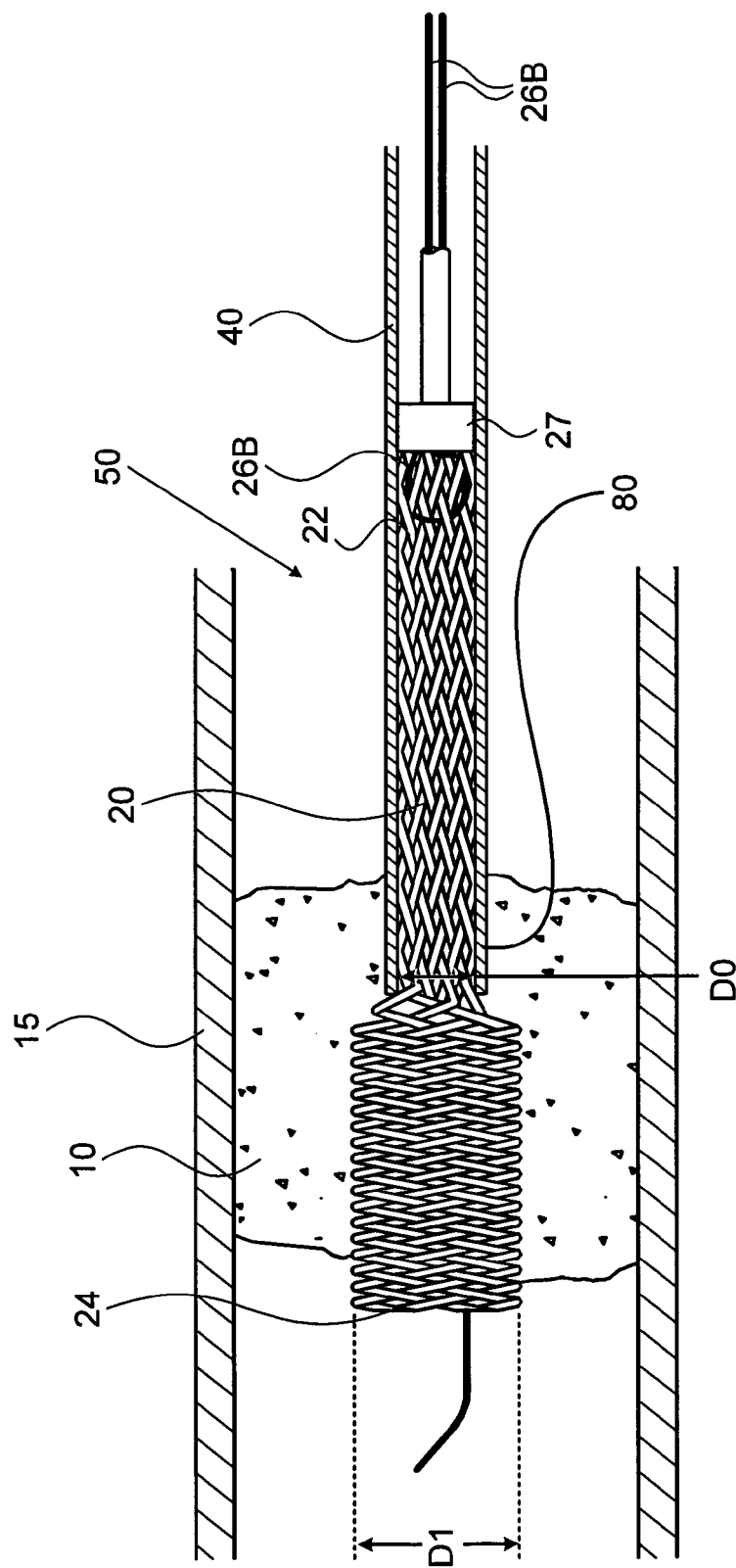

In another embodiment illustrated in FIG. 2E, a member 26B constituted of one of a flexible rod, a filament or a bundle of filaments is attached to proximal end 22 of self expanding device 20. Member 26B can be produced by many different techniques, including but not limited to looping, tying, stitching, interweaving, gluing, welding and soldering, to one or more locations within proximal end 22. In a preferred embodiment member 26B is looped into the collapsible braided construction of proximal end 22 and thus reduces the diameter of self expanding device 20 while tensioned. Self expanding device 20 can be retracted into catheter 40 by tensioning holding member 26B and advancing distal portion 80 of catheter 40 from proximal end 22 to distal end 24 of self expanding device 20. In this particular embodiment a stopper 27 with an outer diameter fits into the inner diameter of catheter 40 and facilitates deployment of self expanding device 20 into occlusion 10 since stopper 27 is in contact with proximal end 22 of self expanding device 20 when retracting catheter 40 out of its position across occlusion 10.

FIG. 3 illustrates a high level schematic diagram of a partially sectioned view of the distal portion of temporary endovascular conduit system 50 of FIG. 1 and a delivery mechanism 70 for intra-arterial administration of t-PA according to an exemplary embodiment, with device 20 illustrated with coating 95. Coating 95 is in some embodiments non-permeable, and in other embodiments permeable. Self expanding device 20 is shown in its large diameter state, i.e. its fully expanded uncompressed state, inside occlusion 10, thereby sustaining at least some blood flow through occlusion 10, as described above. Thus, penumbral tissue preservation is facilitated, thereby prolonging the time window for any effective catheter based recanalization procedure, as described above. In one embodiment, temporary endovascular conduit system 50 is temporarily deployed, so as to supply oxygenated blood to the ischemic penumbrae, and thereafter removed prior to any endovascular procedure for attempting to remove or disrupt occlusion 10, and optionally redeployed between repeated procedures for attempting to remove or disrupt occlusion 10. In another embodiment, as illustrated in FIG. 3, temporary endovascular conduit system 50 is deployed prior to any endovascular procedure for recanalization of lumen 15, and self expanding device 20 remains expanded inside occlusion 10 during the procedure, thereby maintaining blood flow during the procedure. Optionally, coating 95 is permeable, and thus allows for the passage of a fluid from delivery mechanism 70 to occlusion 10. In such an embodiment, delivery mechanism 70 is preferably delivered to be within self expanding device 20 optionally formed of a mesh exhibiting openings such that fluid exiting delivery mechanism 70 is received to the circumference of self expanding device 20 deployed across occlusion 10. In another embodiment catheter 40 is used as a passage of a fluid from outside of the body to the occlusion site eliminating the need for delivery mechanism 70.

Delivery mechanism 70 is manipulated through body lumen 15 from an entry site, such as the femoral artery, to a region proximal to occlusion 10. In the embodiment in which temporary endovascular conduit system 50 has been removed and guidewire 30 has been left in place, delivery mechanism 70 can be manipulated over guidewire 30. In the embodiment in which guidewire 30 has also been removed, or in the embodiment in which temporary endovascular conduit system 50 has not been removed, as illustrated, delivery mechanism 70 can be manipulated over a dedicated additional guidewire and/or through a guiding catheter, or by using any other technique known in the art. Delivery mechanism 70 administers a drug such as a neuro-protective agent, or a thrombolytic agent such as t-PA or any other antithrombotic agent into occlusion 10, thus breaking down occlusion 10. In another embodiment, other means of removing or disrupting occlusion 10, such as: thrombolytic agent infusing techniques; distal or proximal embolectomy devices; various wire corkscrews and baskets; clot capturing devices; and clot aspiration and removing devices, can be used. Other methods of removing or disrupting occlusion 10, such as: facilitating fibrinolysis by an outside energy source such as ultrasound or laser energy; and mechanical manipulation of occlusion 10 by primary angioplasty and/or by employing stents permanently or transiently, may be used.

Figure 4:
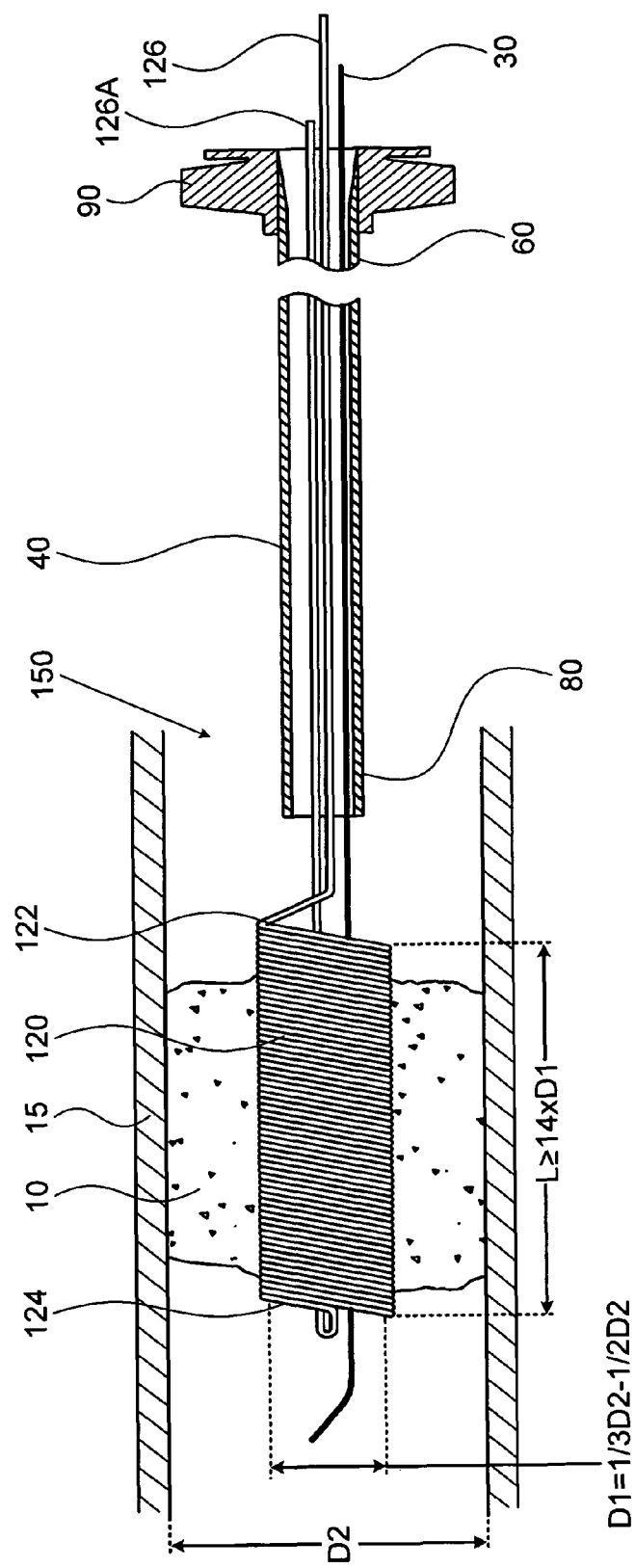
FIG. 4 illustrates a high level schematic diagram of a sectioned view of a second embodiment of a temporary endovascular conduit system, comprising an expanding device.

FIG. 4 illustrates a high level schematic diagram of a sectioned view of a second embodiment of a temporary endovascular perfusion conduit system, denoted temporary endovascular perfusion conduit system 150, deployed in an occlusion 10 occluding a body lumen 15. Temporary endovascular perfusion conduit system 150 comprises: a catheter 40, exhibiting a proximal portion 60 and a distal portion 80; a hub 90; a pair of members 126 and 126A; and an expanding device 120, exhibiting a proximal end 122 and a distal end 124, illustrated in a large diameter state. A guide wire 30 is also provided. The diameter of body lumen 15 in the area of occlusion 10 is denoted D2, and the inner diameter of expanding device 120 in the large diameter state denoted D1, is between ⅓ and ½ of D2. Advantageously providing a conduit exhibiting an inner diameter for blood flow of at least ⅓ of D2 allows a sufficient blood flow, in the absence of sufficient collateral flow from other arteries, to prevent or delay cell death since this provides for a resultant stenosis of less than 75%.

Proximal end 122 of expanding device 120 is positioned proximally to occlusion 10 and distal end 124 of expanding device 120 is positioned distally to occlusion 10. Expanding device 120 in the large diameter state provides a conduit for limited blood flow from proximal end 122 to distal end 124. Optionally, the length of expanding device 120 in the large diameter, denoted L, is at least 5 times D1. In another non-limiting embodiment length L is at least 10 times D1. In another non-limiting embodiment length L is at least 15 times D1. In another non-limiting embodiment length L is at least 20 times D1. In another non-limiting embodiment length L is at least 30 times D1. In one particular non-limiting embodiment length L is at least 14 times D1. Thus, a conduit of sufficient length to extend from a point proximal of occlusion 10 to a point distal of occlusion 10 is provided.

Hub 90 is attached to proximal portion 60 of catheter 40. In one embodiment members 126 and 126A are respectively connected to one or both of proximal end 122 and distal end 124 of expanding device 120. In one particular embodiment member 126 is connected to proximal end 122 of expanding device 120 and member 126A is connected to distal end 124 of expanding device 120, as will be described further hereinto below. Members 126 and 126A and guide wire 30 run through catheter 40 and hub 90 and out therefrom, and are provided to be long enough so as to be accessible.

The structure of expanding device 120 can be of any kind, providing it is hollow, including, but not limited to, a tubular tube, a shield tube and a self expanding structure manufactured by weaving, braiding, laser cutting, or by coiling a filament. Optionally expanding device 120 is a self expandable coiled tubular member, as illustrated, formed by winding a filament spirally and closely over a predetermined diameter and arranged such that when in a fully expanded state each wind is in contact with an adjacent wind, thereby forming a solid tubular shape. The coil forming expanding device 120 can be produced from many different materials, including, but not limited to, metals, polymers and composites. More specifically, these materials can include cobalt-chrome alloys, stainless steel, nylon, and polyesters. In a preferred embodiment, superelastic materials such as some nickel titanium alloys, are used. Further preferably, a formulation of nickel titanium alloy comprising about 51%-56% nickel and about 44%-49% titanium is used. Optionally, expanding device 120 is not self-expandable, but is instead balloon-expandable, shape memory altered by temperature change or externally stretchable without limitation.

In one embodiment the filament comprising expanding device 120 has a round cross section, the diameter of the cross section usually ranging between about 0.001 inches and 0.006 inches and optionally between 0.001 inches and 0.0035 inches. In another embodiment the filament comprising expanding device 120 is a flat wire with a non-circular cross section.

In one embodiment (not shown) the coil forming expanding device 120 is coated with a non-porous elastic material. Coating over the porous coil will form a solid tubular conduit within occlusion 10. The elastic material can be any of a plurality of materials, including, but not limited to: polymers such as silicone, polyethers, polyurethanes, polyamides, hydrogels such as polyvinyl alcohol or polyvinyl pyrrolidone, and other polymers suitable for intravascular use; permeable, semi-permeable and non-permeable membranes; and expandable foams. The elastic material is formed into a fabric mesh and placed around expanding device 120. Optionally, the elastic material is porous, preferably less permeable than expanding device 120.

In the absence of a non-porous elastic material coating any particles from occlusion 10 which pass through the relatively small openings forming expanding device 120 flow out therefrom, thereby avoiding harmful disruption of blood flow or occlusion of a vessel thereof.

Expanding device 120 in the large diameter state, as shown, provides and sustains a conduit exhibiting an inner diameter D1 for sufficient blood flow to the region distal of occlusion 10 and from there to the affected area, thereby reducing the infarction rate of penumbral tissue. As a result, the effective time window for performing endovascular attempts to remove or disrupt occlusion 10 is expanded. Shortening the length and/or increasing the hollow cross-section diameter of expanding device 120 may result in greater cerebral blood flow to the region distal to occlusion 10 and from there to the affected area, resulting in a greater reduction in the infarction rate of penumbral tissue. In one embodiment length L of expanding device 120 in a maximum expanded state is provided to be as short as possible, while being longer than the length of occlusion 10, optionally between 2 mm and 40 mm longer than the length of occlusion 10, and the diameter of the hollow cross-section of expanding device 120 in a maximum expanded state is provided to be between ⅓ and ½ of diameter D2 of body lumen 15, as described above. In one embodiment, where occlusion 10 is 10 mm long, length L is 20 mm, thereby extending 5 mm proximally of occlusion 10 and 5 mm distally of occlusion 10. In another embodiment, where occlusion 10 is 20-30 mm long, length L between 40 mm and 50 mm, thereby extending between 5 mm and 15 mm proximally of occlusion 10 and between 5 mm and 15 mm distally of occlusion 10.

Expanding device 120 provides enough radial force at diameters up to the unstressed maximum expanded state of ½ of D2 so as to prevent movement of expanding device 120 in occlusion 10, while being small enough so as not traumatize the walls of body lumen 15. In one non-limiting embodiment, the inside diameter of expanding device 120 in its maximum expanded state represents a conduit with a cross section of at least 0.685 mm$^2$. When expanding device 120 is at its maximum expanded state it is considered at resting state, since no radial expansion force is exhibited by expanding device 120, in particular expanding device 120 does not urge to expand beyond said second large diameter state. Thus, expanding device 120 may exhibit outward radial force when within occlusion 10, until expansion has reached the unstressed maximum expanded state of ½ of D2. Once expanding device 120 has reached the unstressed maximum expanded state of ½ of D2 no radial force is applied to occlusion 10. Furthermore no radial force is applied to the walls of body lumen 15 distally and proximally of occlusion 10.

Further preferably the hollow cross-sectional area of expanding device 120 is small enough so as to allow simultaneous use of expanding device 120 and a device for dislodging, removing and/or dissolving the clot, as will be described below in relation to FIG. 6.

Optionally, expanding device 120 is secured in location within occlusion 10 by catheter 40 or by another anchoring means secured externally of the patient body, such as by members 126, 126A or 126B to be described further below Optional members 126,126A are provided in order to facilitate the deployment of expanding device 120 into occlusion 10 particularly aiding in control of localization and further procedures, and/or the ultimate retraction of expanding device 120 therefrom. Members 126 and 126A are in one embodiment each constituted of one of a flexible rod, a filament or a bundle of filaments. In one embodiment the cross section of each of members 126 and 126A are on the same order as the cross section of guidewire 30, with guidewire 30 preferably being a 0.014" (0.3556 mm) guidewire known to the art exhibiting a cross-sectional area of less than 0.1 mm$^2$. In the embodiment in which member 126 is connected to proximal end 122 of expanding device 120 and member 126A is connected to distal end 124 of expanding device 120, stretching and compressing of expanding device 120 is enabled by respectively relatively pulling and pushing members 126 and 126A to expand and decrease the length between proximal end 122 and distal end 124. Stretching expanding device 120 reduces its cross-sectional area and enables an operator to change the placement of expanding device 120 easily. Compressing expanding device 120 enlarges its hollow cross-sectional area so as to allow more blood flow there through, as described above. As will be described below in relation to FIG. 5D, expanding device 120 can be retracted into the catheter 40 using members 126, 126A and withdrawn from the patient body along with the retraction of catheter 40.

In another embodiment members 126,126A are inherently connected to expanding device 120, i.e. members 126,126A are thin local elongated protrusions of expanding device 120. There is no requirement that a single catheter 40 be provided for both delivery of expanding device 120 and withdrawal of expanding device 120. In one embodiment, withdrawal of expanding device 120 comprises reduction in radial size to a size greater than the radial size of expanding device when first delivered to occlusion 10.

In order to enable visualization of the coil that forms expanding device 120 under fluoroscopy, in one embodiment numerous radiopaque materials such as gold, platinum, or tungsten can be applied using various methods such as marker, electroplating, ion deposition, and coating. In a preferred embodiment, expanding device 120 is coated with a radiopaque polymer such as silicone mixed with tantalum powder.

Figure 5A:
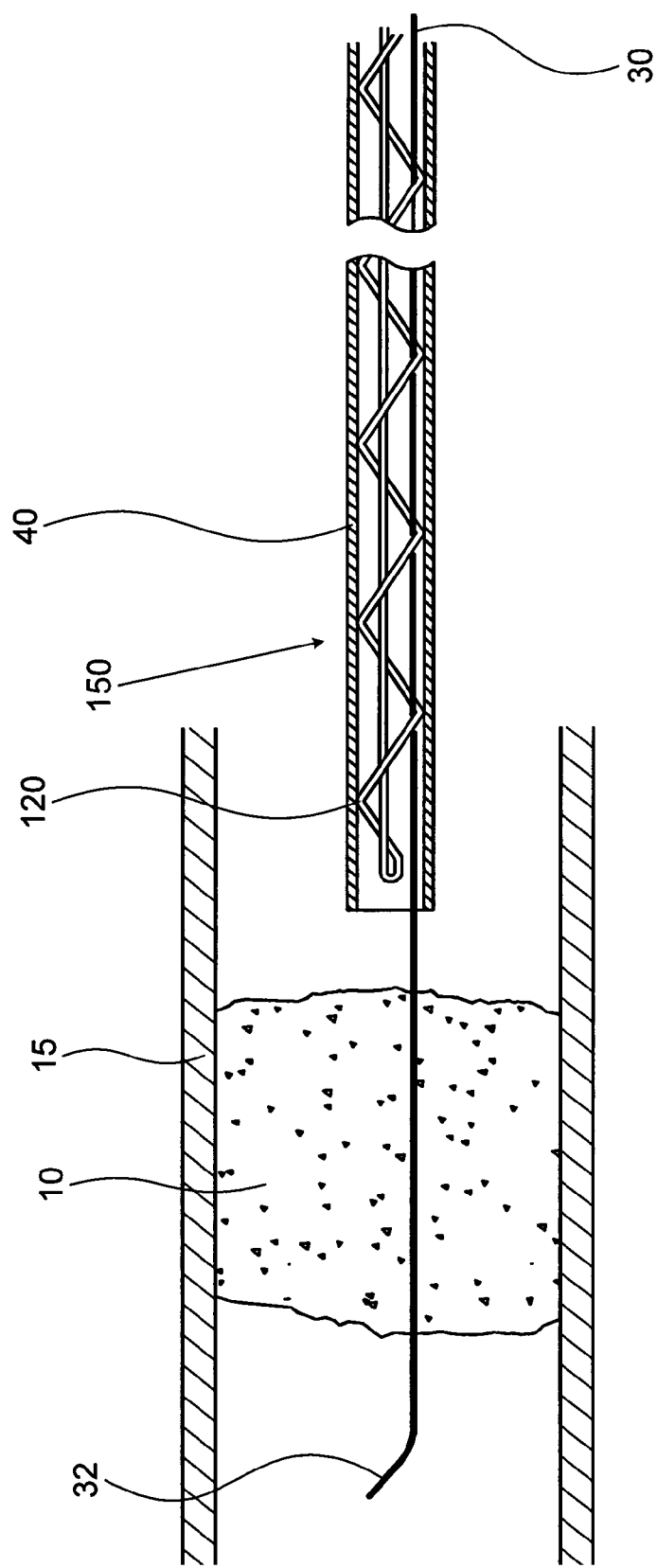
FIGS. 5A-5D illustrate high level schematic diagrams of partially sectioned views of the distal portion of the temporary endovascular perfusion conduit system of FIG. 4, showing sequential steps in the deployment of the expanding device in a vessel according to an exemplary embodiment.

FIGS. 5A-5E illustrate high level schematic diagrams of partially sectioned views of the distal portion of temporary endovascular perfusion conduit system 150 of FIG. 4, showing sequential steps in the deployment of expanding device 120 within body lumen 15 across occlusion 10 according to an exemplary embodiment, the description of FIGS. 5A-5D being taken together. In FIG. 5A expanding device 120 is in a collapsed state, i.e. a small diameter state, and secured within catheter 40, and particulary in a distal portion of catheter 40. Expanding device 120 is pre-loaded or back-loaded onto guidewire 30 while secured within catheter 40. Guidewire 30 is manipulated through body lumen 15 from an entry site, such as the femoral artery, to the region of body lumen 15 occluded by occlusion 10. A distal tip 32 of guidewire 30 is advanced across occlusion 10 using appropriate guidewire and crossing techniques known in the art. Once distal tip 32 of guidewire 30 passes through the distal end of occlusion 10, catheter 40 is advanced through occlusion 10. In one embodiment, after distal tip 32 of guidewire 30 has passed through the distal end of occlusion 10, a micro catheter can be used to visualize the patency of both the vasculature proximal to occlusion 10 and the vasculature distal to occlusion 10 using conventional radiographic techniques, prior to advancing catheter 40 over guidewire 30.

Figure 5B:
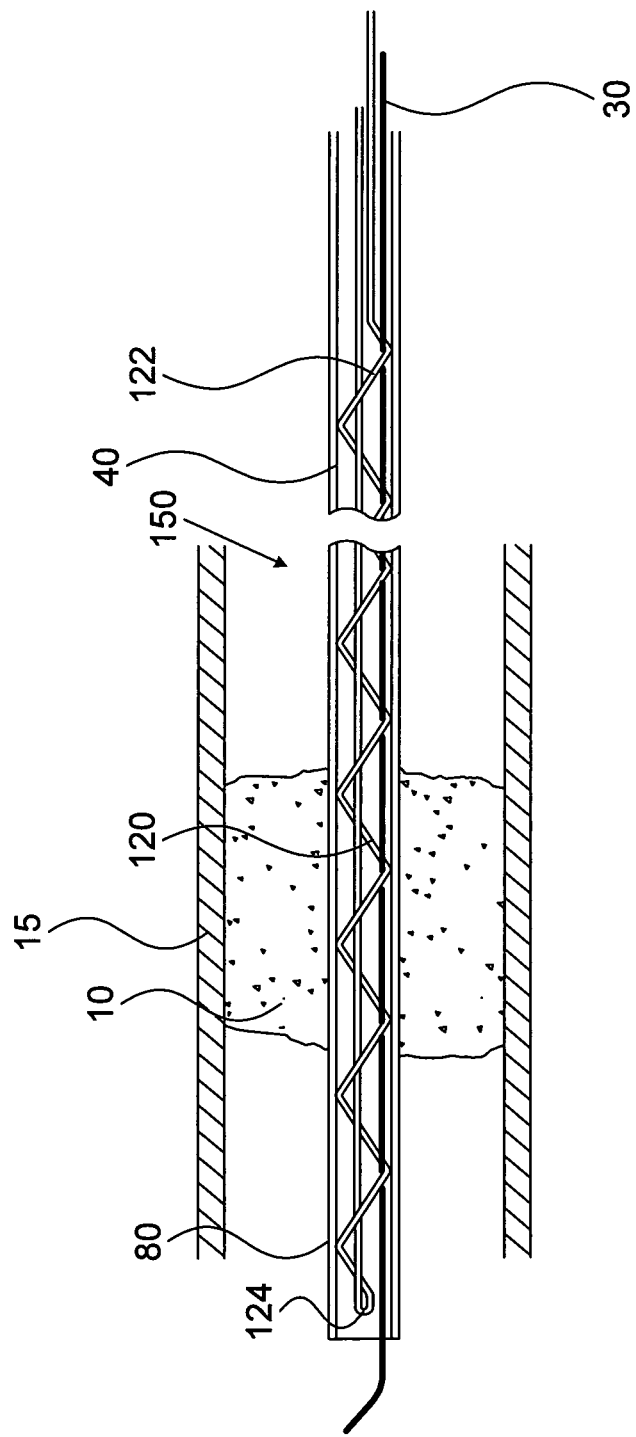

In FIG. 5B temporary endovascular conduit system 150 comprising catheter 40 constraining expanding device 120 is advanced through occlusion 10, with distal portion 80 of catheter 40 and distal end 124 of expanding device 120 extending distally of occlusion 10. In one embodiment, a radiographic solution may be injected through hub 90 of FIG. 4 prior to advancing temporary endovascular conduit system 150 into occlusion 10, thus after the positioning of catheter 40 across occlusion 10 the length of occlusion 10 can be determined, thereby allowing an operator to determine the desired positions of distal end 124 and proximal end 122 of expanding device 120. In another embodiment, determining of the length of occlusion 10 is performed prior to inserting temporary endovascular conduit system 150 in the patient body, thus enabling the operator to choose a specific expanding device 120 with a desired final length and expanded large diameter. Various methods can be applied to visualize proximal end 122 and distal end 124 of expanding device 120 under fluoroscopy, as described above in relation to FIG. 4.

Figure 5C:
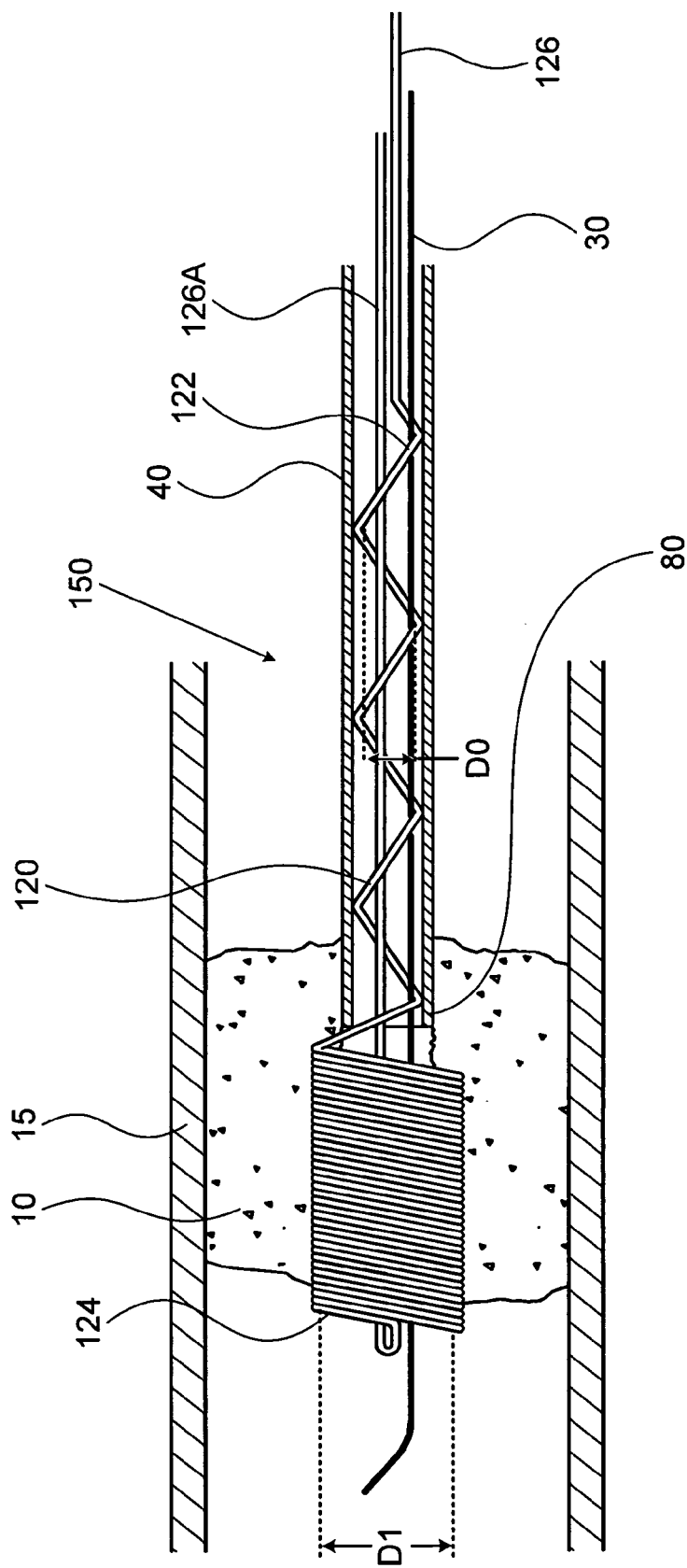

In FIG. 5C catheter 40 is partially retracted from expanding device 120 while members 126,126A are held in place, thereby partially releasing expanding device 120 from catheter 40 through distal portion 80. In the embodiment in which expanding device 120 is self expandable, due to self expanding properties the exposed part of expanding device 120 automatically performs an outward radial expansion and preferably forms into a generally circular configuration. Optionally, inner diameter D1 of expanding device 120 in the large diameter state is no greater than twice, optionally no greater than 1.5 times, and further optionally no greater than 1.2 times the inner diameter of expanding device 120 in the first small diameter state when held within catheter 40, denoted D0.

Figure 5D:
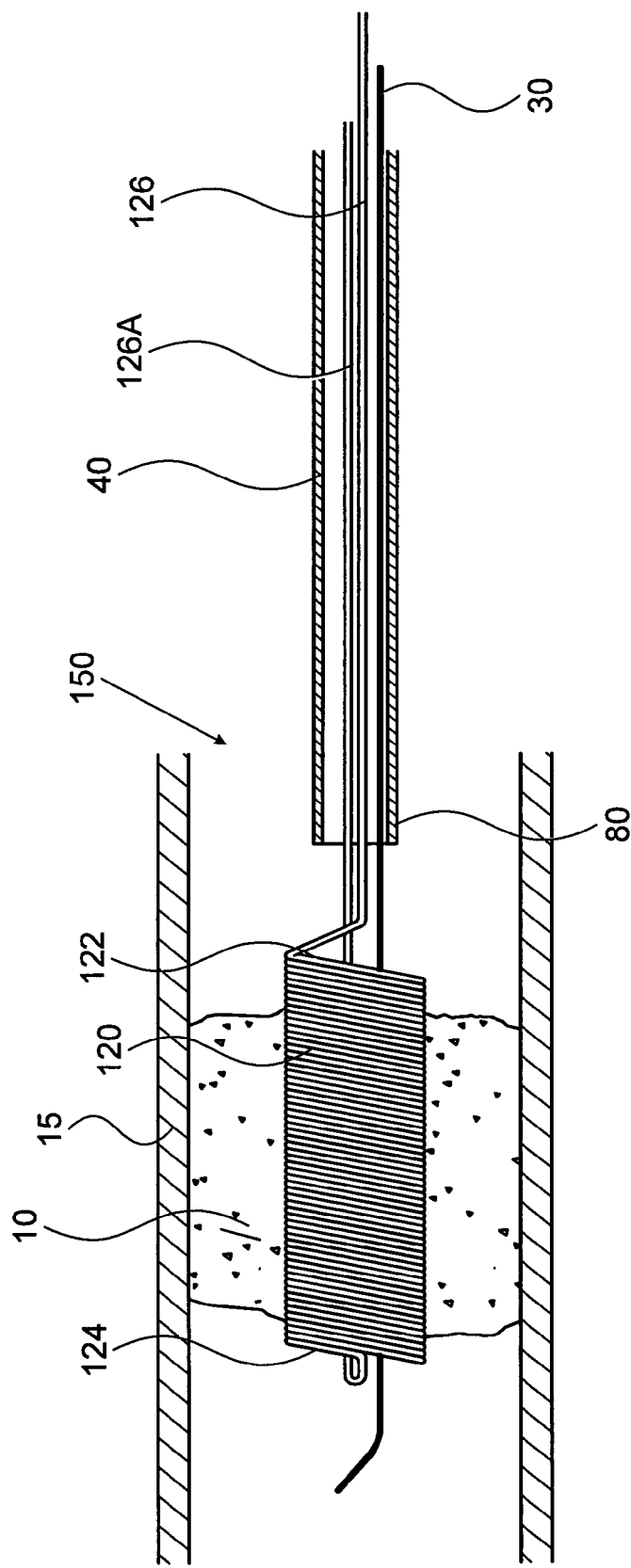

In FIG. 5D catheter 40 is retracted until expanding device 120 is fully released. Expanding device 120 expands to its large diameter state presenting a conduit for blood flow through occlusion 10. Catheter 40 may be fully retracted from the patient body. In one embodiment guidewire 30 remains positioned in occlusion 10 to provide guidance for maneuvering medical means to the site of occlusion 10. In another embodiment guidewire 30 is removed from the patient body and member 126 and/or member 126A provides guidance for maneuvering medical means to the site of occlusion 10, thus enabling extended medical procedures without the need of a guide wire 30.

Temporary endovascular perfusion conduit system 150 can be fully retracted out of the patient body, whenever necessary. In one embodiment this is accomplished by expanding the length of expanding device 120 by manipulation of members 126, 126A thereby reducing the diameter of expanding device 120. Once the diameter of expanding device 120 has been reduced, catheter 40 is preferably advanced over expanding device 120 while expanding device 120 is held in the small diameter state by members 126, 126A, and catheter 40 containing therein expanding device 120 is then removed from the patient body. Alternatively, catheter 40 is held stationary and expanding device 120 in the small diameter state is withdrawn from the area of occlusion 10 towards proximal end 80 of catheter 40, and then drawn within catheter 40. In an alternative embodiment, expanding device 120 is maintained in the small diameter state by the manipulation of members 126, 126A and removed from the patient body by further manipulation of members 126, 126A.

Advantageously, since expanding device 120 may be collapsed and returned within catheter 40, numerous deployments of expanding device 120 at various locations may be performed as a single endovascular procedure.

Figure 5E:
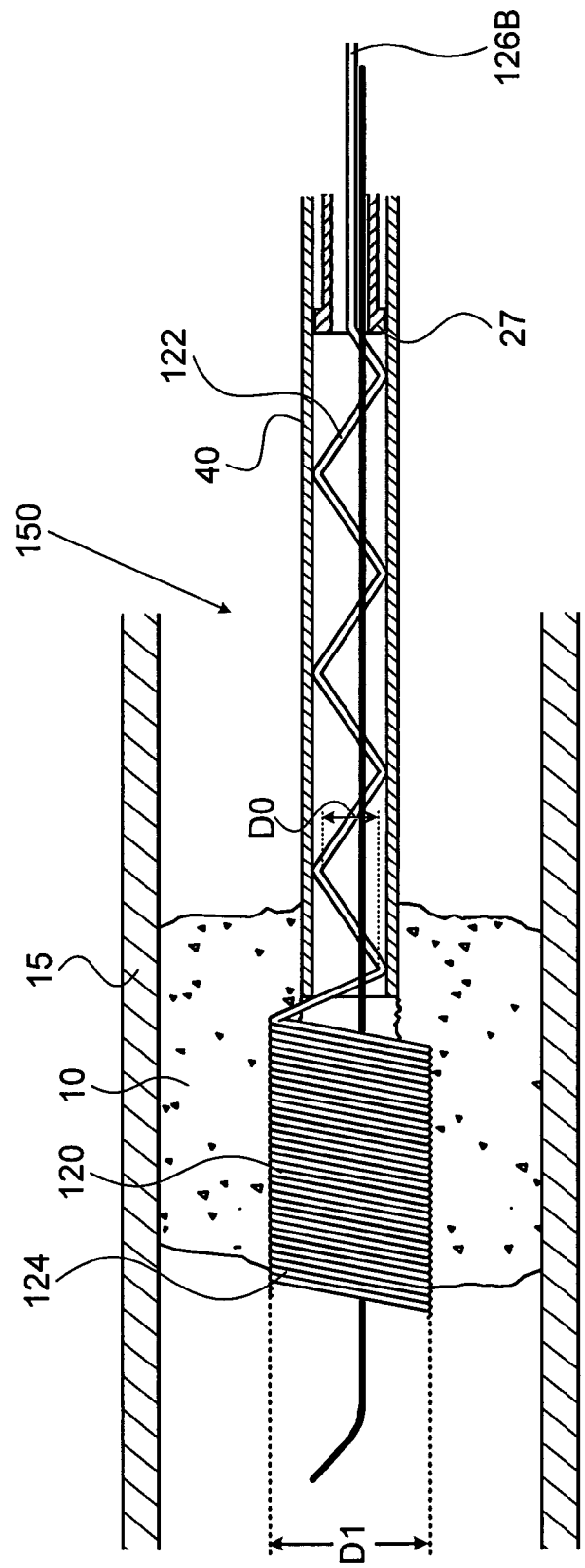

In another embodiment illustrated in FIG. 5E, expanding device 120 can be retracted into catheter 40 by a holding member 126B by tensioning holding member 26B and advancing distal portion 80 of catheter 40 from proximal end 122 to distal end 124 of expanding device 120. In this particular embodiment a stopper 27 exhibiting an outer diameter fits into the inner diameter of catheter 40 and facilitates the deployment of expanding device 120 into occlusion 10 by keeping stopper 27 in constant contact against the proximal end 122 of expanding device 120 and pushing it gradually during the retraction of catheter 40 out of its position across occlusion 10.

Figure 6:
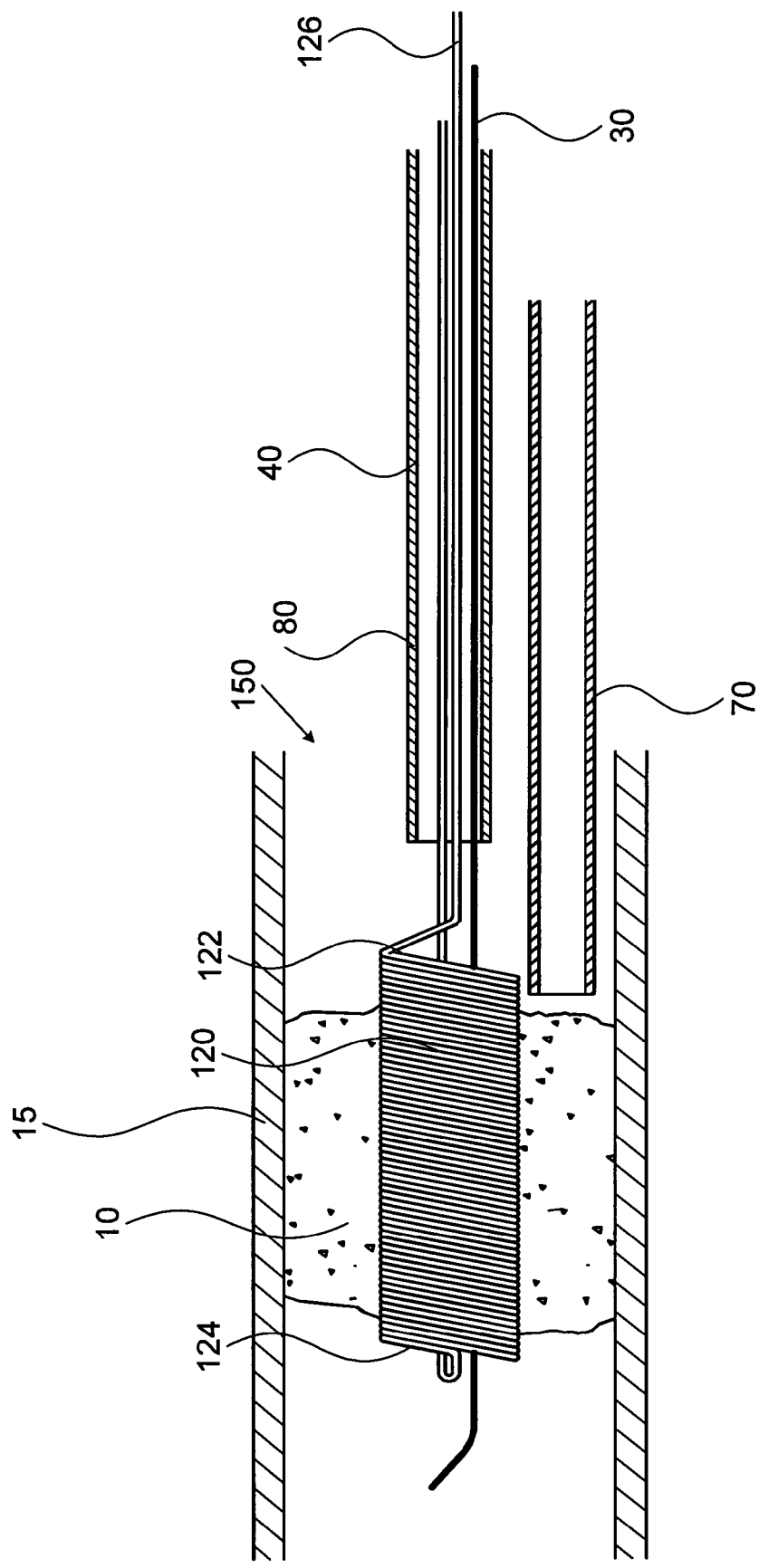
FIG. 6 illustrates a high level schematic diagram of a partially sectioned view of the distal portion of the temporary endovascular perfusion conduit system of FIG. 4 and a delivery mechanism for intra-arterial administration of a medicament according to an exemplary embodiment.

FIG. 6 illustrates a high level schematic diagram of a partially sectioned view of the distal portion of temporary endovascular perfusion conduit system 150 of FIG. 4 and a delivery mechanism 70 for intra-arterial administration of t-PA according to an exemplary embodiment. Expanding device 120 is shown in its large diameter state, i.e. its fully expanded uncompressed state, inside occlusion 10, thereby sustaining at least some blood flow through occlusion 10, as described above. Thus, penumbral tissue preservation is facilitated, thereby prolonging the time window for any effective catheter based recanalization procedure, as described above. In one embodiment, temporary endovascular perfusion conduit system 150 is temporarily deployed, so as to supply oxygenated blood to the ischemic penumbrae, and thereafter removed prior to any endovascular procedure for attempting to remove or disrupt occlusion 10, and optionally redeployed between repeated procedures for attempting to remove or disrupt occlusion 10. In another embodiment, illustrated in FIG. 6, temporary endovascular perfusion conduit system 150 is deployed prior to any endovascular procedure for attempting to remove or disrupt occlusion 10, and expanding device 120 remains expanded inside occlusion 10 during the procedure, thereby maintaining blood flow during the procedure. Optionally, expanding device 120 is permeable, and thus allows for the passage of a fluid from delivery mechanism 70 to occlusion 10. In such an embodiment, delivery mechanism 70 is preferably delivered to be within expanding device 120 optionally formed as a spiral winding wherein successive turns are not in contact with previous turns thus forming a structure such that fluid exiting delivery mechanism 70 is received to the circumference of expanding device 120 deployed across occlusion 10. In another embodiment catheter 40 is used as a passage of a fluid from outside of the body to the occlusion site eliminating the need for delivery mechanism 70.

Delivery mechanism 70 is manipulated through body lumen 15 from an entry site, such as the femoral artery, to a region proximal to occlusion 10. In the embodiment in which temporary endovascular perfusion conduit system 150 has been removed and guidewire 30 has been left in place, delivery mechanism 70 can be manipulated over guidewire 30. In the embodiment in which guidewire 30 has also been removed, or in the embodiment in which temporary endovascular perfusion conduit system 150 has not been removed, as illustrated, delivery mechanism 70 can be manipulated over a dedicated additional guidewire and/or through a guiding catheter, or by using any other technique known in the art. Delivery mechanism 70 administers a drug such as a neuro-protective agent, or a thrombolytic agent such as t-PA, or any other antithrombotic agent, into occlusion 10, thus breaking down occlusion 10. In another embodiment, other means of removing or disrupting occlusion 10, such as: thrombolytic agent infusing techniques; distal or proximal embolectomy devices; various wire corkscrews and baskets; clot capturing devices; and clot aspiration and removing devices, can be used. Other methods of removing or disrupting occlusion 10, such as: facilitating fibrinolysis by an outside energy source such as ultrasound or laser energy; and mechanical manipulation of occlusion 10 by primary angioplasty and/or by employing stents permanently or transiently, may be used.

Figure 7A:
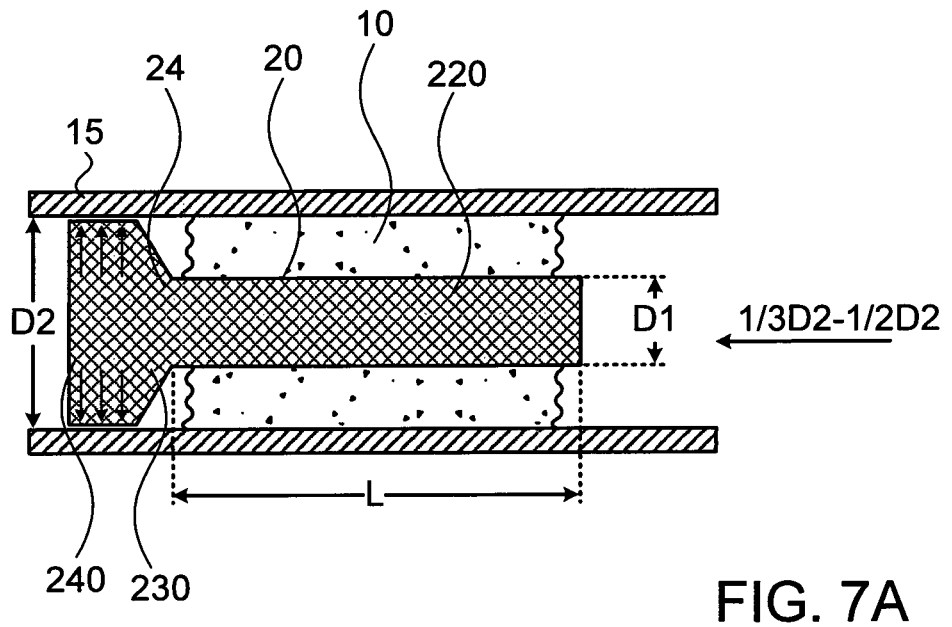
FIG. 7A illustrates a high level schematic diagram of a sectioned view of an embodiment of a temporary endovascular perfusion conduit exhibiting a distal filtering extension member.

FIG. 7A illustrates a high level schematic diagram of a sectioned view of an embodiment of a temporary endovascular perfusion conduit 220 exhibiting a distal filtering extension member 240, coupled to distal end 24 of self expanding device 20 via transition portion 230. Self expanding device 20 is substantially as described above in relation to FIG. 1, exhibiting an inner diameter between ⅓ and ½ of D2, i.e. the diameter of body lumen 15 in the area of occlusion 10. In an exemplary embodiment distal filtering extension member 240 is sized so as to meet the inner walls of lumen 15 in the area distal of occlusion 10. In an exemplary embodiment, distal filtering extension member 240 is arranged to be at the resting state for diameters of 0.25 mm-1.5 mm larger than the inner walls of lumen 15 in the area distal of occlusion 10, thus ensuring that distal filtering extension member 240 meets the inner walls of lumen 15 and further optionally provides a securing or anchoring functionality. Transition portion 230 is optionally a flared portion, and both transition portion 230 and distal filtering extension member 240 may be provided in a single integrated braid using an appropriately shaped mandrel, as described in U.S. Pat. No. 7,093,527 issued Aug. 22, 2006 to Rapaport et al, entitled "Method and Apparatus for Making Intraluminal Implants and Construction Particularly Useful in such Method and Apparatus", the entire contents of which is incorporated herein by reference. In an exemplary embodiment, distal filtering extension member 240 is arranged to trap particles greater than a predetermined size. In one preferred embodiment the predetermined size is 500 microns. In another embodiment the predetermined size is 350 microns. In another embodiment the predetermined size is 200 microns, and in yet another embodiment the predetermined size is 80 microns.

In another embodiment transition portion 230 and distal filtering extension member 240 are of a different element than that of temporary endovascular perfusion conduit 220, such as of silicon or rubber. The distal portion of distal filtering extension member 240 may be open, may exhibit a filter, or be closed in the area opposing transition portion 230 without exceeding the scope. The filter of distal filtering extension member 240 may be more or less permeable than the walls of temporary endovascular perfusion conduit 220 without exceeding the scope.

Figure 7B:
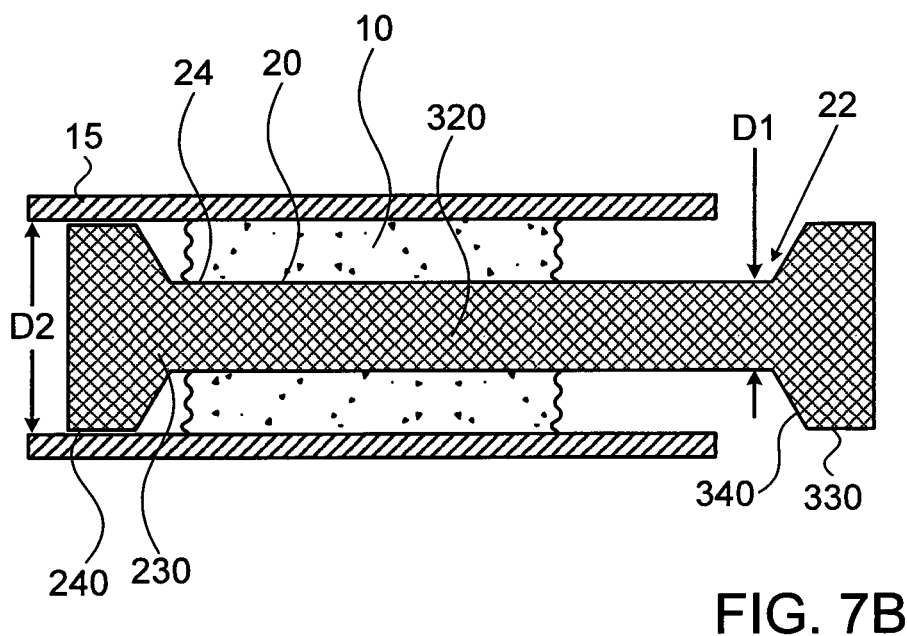
FIG. 7B illustrates a high level schematic diagram of a sectioned view of an embodiment of a temporary endovascular perfusion conduit exhibiting a proximal securing member and a distal filtering extension member.

FIG. 7B illustrates a high level schematic diagram of a sectioned view of an embodiment of a temporary endovascular perfusion conduit 320 exhibiting distal filtering extension member 240 coupled to distal end 24 of self expanding device 20 via transition portion 230, and further exhibiting a proximal securing member 330 coupled to proximal end 22 of self expanding device 20 via a transition portion 340. Self expanding device 20 is substantially as described above in relation to FIG. 1, exhibiting an inner diameter between ⅓ and ½ of D2, i.e. the diameter of body lumen 15 in the area of occlusion 10 and distal filtering extension member 240 is substantially as described above in relation to FIG. 7A.

Proximal securing member 330 is preferably sized so as to meet the inner walls of lumen 15 in the area proximal of occlusion 10, thus occlusion 10 is completely encased by the combination of self expanding device 20, distal filtering extension member 240 and proximal securing member 330. In an exemplary embodiment, proximal securing member 330 is arranged to be at resting state for diameters of 0.25 mm-1.5 mm larger than the inner walls of lumen 15 in the area proximal of occlusion 10, thus ensuring that proximal securing member 330 meets the inner walls of lumen 15, thus securing particles detached from occlusion 10 to flow out therefrom, thereby avoiding harmful disruption of blood flow or occlusion of a vessel thereof, and optionally providing a securing or anchoring functionality. Transition portion 340 is preferably a flared portion, and both transition portion 340 and proximal securing member 330 may be provided in a single integrated braid using an appropriately shaped mandrel, as described in U.S. Pat. No. 7,093,527 incorporated above by reference.

Figure 8:
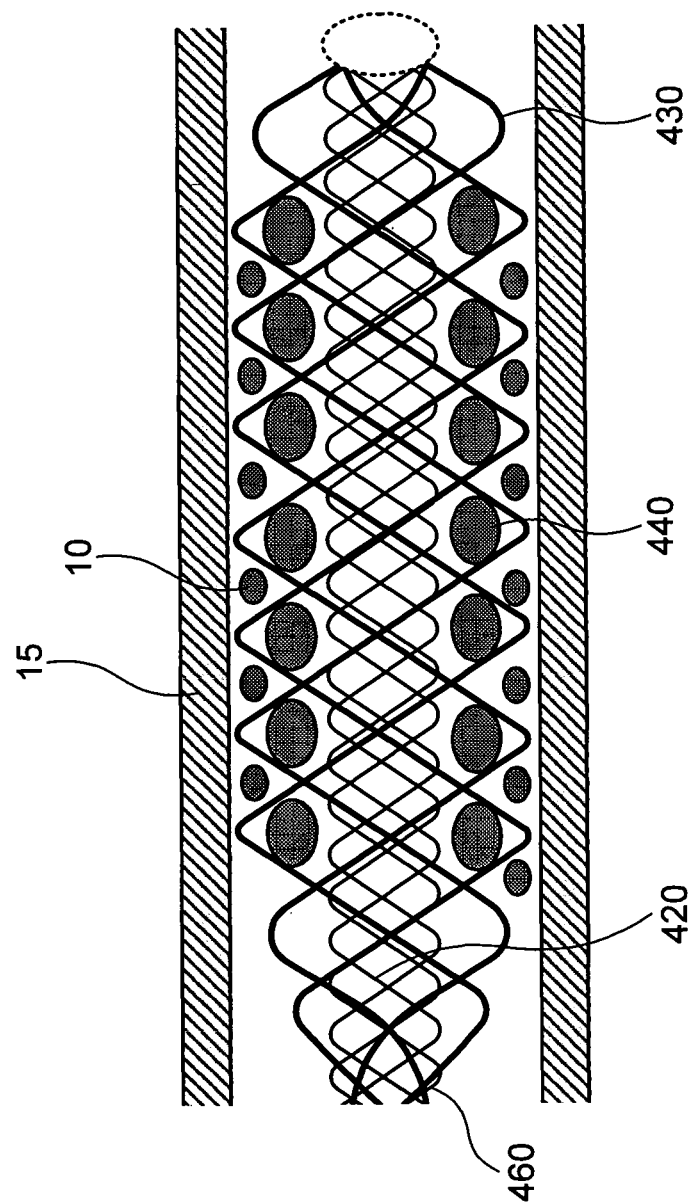
FIG. 8 illustrates a high level schematic diagram of a sectioned view of an embodiment of a temporary endovascular perfusion conduit comprising a clot retrieval device.

FIG. 8 illustrates a high level schematic diagram of a sectioned view of an embodiment of a temporary endovascular perfusion conduit 420 comprising a clot retrieval device 430 in communication with self expanding device 20 shown disposed within body lumen 15 at occlusion 10. Self expanding device 20 is in all respects similar to self expanding device 20 of FIG. 1, with the addition of clot retrieval device 430 constituted of an additional braid external to that of self expanding device 20. Clot retrieval device 430 is arranged to be at resting state for diameters of 0.5 mm-1.5 mm larger than the inner walls of lumen 15 in the area distal of occlusion 10, thus meet the inner walls of body lumen 15.

Clot retrieval device 430 is in an exemplary embodiment an open braid having ½ or less of the number of filaments constituting self expanding device 20, and thus expands to trap within clot retrieval device 430 portions 440 of occlusion 10. Retrieval of clot retrieval device 430, preferably in combination with retrieval of self expanding device 20 thus removes at least a portion of occlusion 10 from body lumen 15 while providing and/or sustaining a conduit for blood passage having a diameter for sufficient blood flow to the region distal of occlusion 10. In one embodiment, not shown for simplicity, distal filtering extension member 240, described above in relation to FIG. 7A is further provided. Additionally, or optionally, axial motion of clot retrieval device 430 may break apart a portion of occlusion 10. Preferably, in such an embodiment clot retrieval device 430 is provided in cooperation with distal filtering extension member 240 of FIG. 7A, thus distal filtering extension member 240 is arranged to trap any portions of occlusion 10 which have been broken apart by clot retrieval device 430.

Production of temporary endovascular perfusion conduit 420 is in one embodiment performed by braiding self expanding device 20 with additional filaments coupled to inherent structural filaments of self expanding device 20, the additional filaments will ultimately appear only in clot retrieval device 430. Section 450 of self expanding device 20 is braided, and the additional filaments are removed from the braiding machine, so that the balance of self expanding device 20 will not exhibit the additional filaments. Braiding of self expanding device 20 continues up to section 460.

As self expanding device 20 is braided to section 460, the filaments of self expanding device 20 are removed from the braiding machine, and a tube with an inner diameter larger than that of self expanding device 20 and an outer diameter of the desired size at the resting state of clot retrieval device 430 is placed over the braided portion of self expanding device 20. The additional filaments of portion 450 are then braided over the tube, up to section 460. The tube is then removed, and all filaments, including the filaments of self expanding device 20 and the additional filaments are braided to completely form section 460.

The above has been described in an embodiment in which temporary endovascular perfusion conduit 420 is a braided device, however this is not meant to be limiting in any way. In another embodiment temporary endovascular perfusion conduit 430 is manufactured by any one of weaving, coiling and laser cutting.

Figure 9:
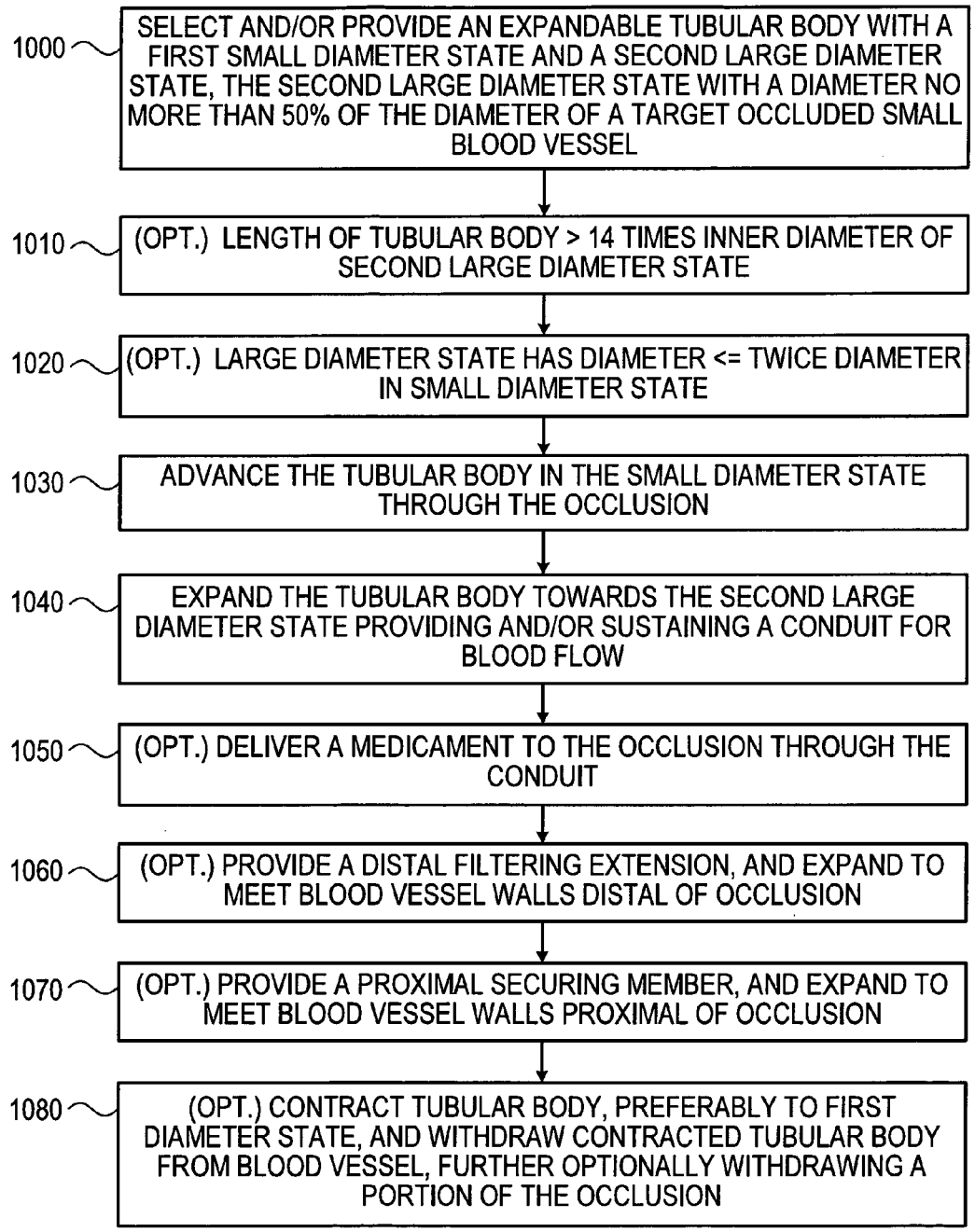
FIG. 9 illustrates a high level flow chart of a method of providing temporary endovascular perfusion and optional clot retrieval.

FIG. 9 illustrates a high level flow chart of a method of providing temporary endovascular perfusion and optional clot retrieval. In stage 1000, an expandable tubular body is provided, preferably selected so as to exhibit a first small diameter state and a second large diameter state. The expandable tubular body exhibits a diameter in the second large diameter state no more than 50% of the diameter of a target blood vessel at the sight of the occlusion.

In optional stage 1010, the length of the expandable tubular body of stage 1000 is selected so as to be at least 14 times the inner diameter of the expandable tubular body in the second large diameter state. In optional stage 1020, the inner diameter of the expandable tubular body of stage 1000 in the large diameter state is selected so as to be no greater than twice the diameter of the expandable tubular body of stage 1000 in the small diameter state. The inner diameter of the small diameter state may not be inherent, and in an exemplary embodiment is defined by the parameters of the delivery catheter, such as catheter 40.

In stage 1030, the expandable tubular body of stage 1000 is advanced in the small diameter state through the occlusion. Alternatively or additionally, a distal portion or a tip of the catheter is first broached through the occlusion thereby opening and/or widening a passage therethrough, later to be occupied and sustained by the expandable tubular body, as the catheter is further advanced. Optionally, the expandable tubular body is manipulated through the body and advanced through the occlusion while loaded onto the distal portion of a delivery catheter, such as catheter 40.

In stage 1040, the advanced tubular body of stage 1030 is expanded towards the second large diameter state, thus providing a conduit through the expanded tubular body to maintain blood flow patency through the occlusion. There is no requirement that the expansion be complete to the second large diameter state, and the only requirement is that sufficient blood flow patency is restored by providing blood flow of at least 25% of the unoccluded blood flow volume. Advantageously, by proper selection of the second large diameter state no additional radial force is supplied by the expanded tubular body to the occlusion, thus preventing unintended and uncontrolled break up.

In optional stage 1050, a medicament is delivered to the occlusion. Preferably the tubular body is permeable by the medicament when in the second large diameter state and thus the medicament is delivered through the tubular body to the occlusion surrounding the tubular body.

In optional stage 1060, a distal filtering extension is provided distal of the tubular body of stage 1000, the distal filtering extension being expanded to meet the blood vessel walls distal of the occlusion. Advantageously, the distal filtering extension traps any dislodged fragments of the occlusion.

In optional stage 1070, a proximal securing mechanism is provided proximal of the tubular body of stage 1000, the proximal securing mechanism being expanded to meet the blood vessel walls proximal of the occlusion. Advantageously, the proximal securing mechanism secures the occlusion and its potentially damaging fragments from dislodging and proceeding further into the bloodstream.

In option stage 1080, the tubular body is contracted, preferably to the first diameter state, and withdrawn from the blood vessel. Optionally, a portion of the occlusion is withdrawn along with the tubular body.

Thus the present embodiments enable a conduit system passively perfusing oxygenated blood through an obstructing clot and allowing for clot retrieval. This is accomplished in certain embodiments by inserting the conduit system into an occluded blood vessel providing for at least partial blood flow through the occluded blood vessel, thereby reducing the infarction rate of penumbral tissue. In one embodiment this is achieved by providing a conduit system exhibiting a collapsible conduit. The conduit system is placed inside the clot occluding the occluded blood vessel. The collapsible conduit is then expanded, forming a conduit inside the clot, thereby allowing at least partial blood flow therethrough.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. A device positionable within a small intracranial blood vessel exhibiting an occlusion caused by a thrombosis or an embolism, the device comprising a self expandable tubular body, said tubular body configured to be constrained in a first small diameter state for manipulation to, and through, the occlusion of the small blood vessel, and a second large diameter state for when said tubular body is deployed within the occlusion, a delivery catheter for delivery of said tubular body;

said device comprising a first member coupled to a proximal end of said tubular body, and a second member coupled to a distal end of said tubular body, said members pullable and pushable relative to each other to change a cross sectional area of said tubular body after self-expansion thereof;

wherein at least a portion of said first member is an integral part of said self expandable tubular body, formed as a local elongated protrusion of said self expandable tubular body; wherein said first member is extendable through the delivery catheter, running through the catheter and out of a proximal end thereof; wherein said second member comprises a filament that extends distally beyond said distal end of said tubular body; and wherein said first and second members are movable with respect to each other to compress said tubular body to increase its diameter or stretch said tubular body to decrease its diameter.

2. The device according to claim 1, wherein the tubular body in said second large diameter state does not urge to expand beyond 50% of the diameter of the small blood vessel.

3. The device according to claim 1, wherein the tubular body in the second large diameter state exhibits a length at least 14 times the inner diameter of the tubular body in the second large diameter state.

4. The device according to claim 1, wherein the tubular body in the second large diameter state exhibits an inner diameter no more than twice the inner diameter of the tubular body in the first small diameter state.

5. The device according to claim 1, further comprising a distal filtering extension coupled to said distal end of said tubular body.

6. The device according to claim 5, wherein the distal filtering extension is arranged to expand to meet the inner wall of the small blood vessel distal of said occlusion.

7. The device according to claim 1, further comprising a proximal securing member coupled to a proximal end of said tubular body, said proximal securing member arranged to expand to meet the inner wall of the small blood vessel.

8. The device according to claim 1, wherein in said collapsed, first diameter state said device is retractable to be withdrawn by pulling on said first member.

9. The device according to claim 1, wherein the device is coated with an elastic non-porous material.

10. The device according to claim 1, wherein the device is constituted of self expanding braided filaments.

11. The device according to claim 1, further comprising a clot retrieval device arranged to retrieve at least a portion of the occlusion, said clot retrieval device in communication with said tubular body and exhibiting a diameter greater than 50% of the diameter of the small blood vessel at the occlusion location.

12. The device according to claim 11, wherein said clot retrieval device comprises a braid external to said tubular body, said braid adapted to trap at least a portion of the occlusion when said tubular body is expanded within said occlusion.

13. The device according to claim 12, wherein said tubular body comprises filaments, and said clot retrieval body comprises 50% or less filaments than said tubular body.

14. The device according to claim 1, wherein the tubular body is coated with an elastic porous material.

15. The device according to claim 1, wherein a medicament is delivered to the occlusion through the device when the device is expanded to the second large diameter state within the occlusion.

16. The device according to claim 1, wherein both of said members extend throughout the delivery catheter and are long enough to be accessible to a user for actuating at least one of said pulling or pushing while said device is inside the body.

17. The device according to claim 1, wherein at least one of said members is configured for delivering medical means to the site of the occlusion.

18. The device according to claim 1, wherein said device is arranged to sustain at least partial patency of a small blood vessel exhibiting an occlusion.

19. The device according to claim 1, wherein in said second large diameter state said device presents a conduit through said tubular body for blood to flow through the occlusion.

20. The device according to claim 1, wherein the inner dimensions of said second large diameter state are no more than 50% of the diameter of the small blood vessel at the occlusion location.

21. The device according to claim 1, wherein said second member comprises a cross sectional area smaller than 0.1 mm^2.

22. The device according to claim 1, wherein said tubular body is configured to be maintained in said second large diameter state using said first and second members, wherein in said second large diameter state said tubular body is expanded only enough to engage said occlusion to withdraw at least a portion of said occlusion between said tubular body and a wall of said small blood vessel.

23. The device according to claim 1, wherein said second member is integrally attached to said distal end of said tubular body.

24. The device according to claim 1, wherein said first and second members are pullable and pushable relative to each other to selectively increase a cross sectional area of said tubular body when said tubular body is in said self-expanded state.

25. The device according to claim 1, wherein said members are pullable and pushable relative to each other to increase and decrease a cross sectional area of said tubular body.

26. The device according to claim 1, wherein said tubular body exhibits an outward radial force sufficient to capture at least a portion of said occlusion between said tubular body and inner walls of a lumen of said blood vessel, said outward radial force small enough so as to not traumatize the walls of said blood vessel.

27. The device according to claim 26, wherein said occlusion decreases a diameter of said inner walls by at least 75%.

28. The device according to claim 1, wherein said first member is interweaved to said proximal end of said self expandable tubular body.

29. The device according to claim 1, wherein said first member is looped into a braided construction of said proximal end of said self expandable tubular body.

30. The device according to claim 1 wherein said tubular body provides enough radial force at diameters up to said second large diameter state so as to prevent movement of said tubular body in said occlusion while being small enough so as not to traumatize the walls of said blood vessel.

31. The device according to claim 1, wherein a distal end of said second member defines a distal-most end of said device.

* * * * *